United States Patent [19]

Schröck et al.

[11] 4,107,304
[45] Aug. 15, 1978

[54] OXO-IMIDAZOLIDINE SUBSTITUTED CEPHALOSPORINS AND ANTIBACTERIAL COMPOSITIONS AND METHODS OF COMBATTING BACTERIA EMPLOYING THEM

[75] Inventors: Wilfried Schröck; Hans-Bodo Konig; Michael Preiss; Karl Georg Metzger, all of Wuppertal; Michael Walkowiak, Cologne, all of Germany

[73] Assignee: Bayer Aktiengesellschaft, Leverkusen, Germany

[21] Appl. No.: 590,794

[22] Filed: Jun. 27, 1975

Related U.S. Application Data

[63] Continuation-in-part of Ser. No. 548,347, Feb. 10, 1975, abandoned.

[30] Foreign Application Priority Data

Feb. 18, 1974 [DE] Fed. Rep. of Germany ....... 2407715

[51] Int. Cl.$^2$ ................ A61K 31/545; C07D 501/34; C07D 501/24
[52] U.S. Cl. ........................................ 424/246; 544/28
[58] Field of Search .................... 260/243 C; 424/246; 426/532; 544/28

[56]    References Cited
        U.S. PATENT DOCUMENTS

| 3,687,949 | 8/1972 | Holdrege | 260/243 C |
| 3,741,962 | 6/1973 | Breuer | 260/243 C |
| 3,860,591 | 1/1975 | Breuer | 260/243 C |
| 3,865,819 | 2/1975 | DeMarinis et al. | 260/243 C |
| 3,956,292 | 5/1976 | Cooper | 260/243 C |
| 3,966,709 | 6/1976 | Konig et al. | 260/239.1 |

FOREIGN PATENT DOCUMENTS 7,407,815  12/1974  Netherlands.

OTHER PUBLICATIONS

Chem. Abstracts vol. 60 (1964) p. 1878.

Primary Examiner—Donald G. Daus
Assistant Examiner—Diana G. Rivers
Attorney, Agent, or Firm—Burgess, Dinklage & Sprung

[57]    ABSTRACT

Cephalosporins of the formula their pharmaceutically-acceptable, nontoxic salts, and hydrates thereof are produced, wherein
A is hydrogen; unsubstituted or substituted alkyl; aryl; or $R_1$—X—, wherein
  X is —CO— or —$SO_2$—, and
  $R_1$ is hydrogen, unsubstituted or substituted alkyl; aryl; thienyl; furyl; amino; alkylamino; dialkylamino; pyrrolidyl; or piperidyl;
or when
  X is —CO—,
  $R_1$ can also be alkoxy;
B is phenyl, methylphenyl, chlorophenyl, hydroxyphenyl or the moiety E is hydrogen, hydroxyl or acetoxy; and
*C is a center of chirality.
These compounds are particularly useful for their antimicrobial and, particularly, antibacterial effects.

20 Claims, No Drawings

OXO-IMIDAZOLIDINE SUBSTITUTED CEPHALOSPORINS AND ANTIBACTERIAL COMPOSITIONS AND METHODS OF COMBATTING BACTERIA EMPLOYING THEM

CROSS-REFERENCE

This is a continuation-in-part of Ser. No. 548,347, filed Feb. 10, 1975, now abandoned.

DETAILED DESCRIPTION

The present invention relates to cephalosporins, a process for their production, pharmaceutical compositions utilizing said compounds, either alone or in combination with other antibiotics, methods of treating bacterial infections in humans and animals utilizing said compounds either alone or in combination with known antibiotics, animal feedstuffs and growth-promoting agents.

It is known in the art that certain acetamidocephalosporanic acids such as cephaloglycine, which carry an aryl radical and an amino group in the α-position of the acetamido group, may be produced by synthetic methods and can be used as antibacterial agents. (See German Offenlegungsschriften 1,670,625, 1,795,188 and 1,795,292; U.S. Pat. Nos. 3,303,193, 3,352,858, 3,485,819 and 3,634,416; Japanese Patent Application 16,871/66; and British Patent No. 1,073,530.) However, these compounds are not active against infections which are caused by bacteria from the genus Pseudomonades.

More particularly, the present invention relates to cephalosporins of the formula

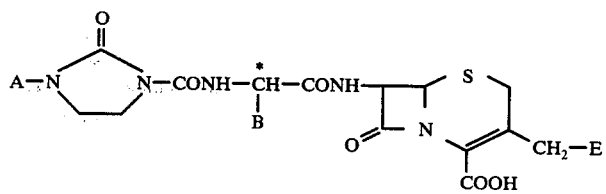

(I)

or a pharmaceutically-acceptable, nontoxic salt thereof, or a hydrate thereof, or said compound in an anhydrous form,
wherein
A is hydrogen; alkyl, especially of 1 to 4 carbon atoms, unsubstituted or substituted by 1 to 5, especially 1 to 3, of the same or different substituents selected from the group consisting of halo, cyano and nitro; aryl, especially of 6 to 10 carbon atoms; or the moiety $R_1$—X—, wherein
X is —CO— or —$SO_2$—, and
$R_1$ is hydrogen; alkyl, especially of 1 to 4 carbon atoms, unsubstituted or substituted by 1 to 5, especially 1 to 3, of the same or different substituents selected from the group consisting of halo, cyano and nitro, or by the moiety $R_2$—$SO_2$ wherein $R_2$ is alkyl of 1 to 4 carbon atoms; aryl, especially of 6 to 10 carbon atoms; thienyl; furyl; amino; alkylamino, especially of 1 to 4 carbon atoms in the alkyl moiety; dialkylamino, especially of 1 to 4 carbon atoms in the alkyl moiety; pyrrolidyl; or piperidyl; and when
X is —CO—,
$R_1$ can also be alkoxy of 1 to 4 carbon atoms;
B is phenyl, methylphenyl, chlorophenyl, hydroxyphenyl or

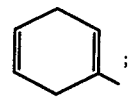

E is hydrogen, hydroxyl or acetoxy; and
Ċ is a center of chirality.
Ċ, which constitutes the chirality center, can be in either of the two possible R- and S- configurations or in the RS- configuration, which includes mixtures of the various diastereomers.

The compounds of the present invention are particularly useful for their strong antimicrobial and, particularly, antibacterial activity.

The compounds of the present invention may be produced by reacting a compound of the formula

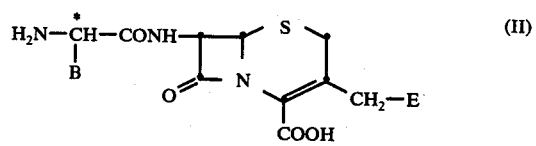

(II)

wherein

B, E and Ċ are as above defined, with a compound of the formula

(III)

wherein
A is as above defined and
W is halogen, azido, phenoxy, nitrophenoxy, dinitrophenoxy, halogenophenoxy of 1 to 5 halogen moieties, or benzylthio,
in the presence of a base, and, in the case of the salts, reacting the free acid produced with a suitable base, and recovering the compound produced.

If cephaloglycine and 1-chloro-carbonyl-2-oxoimidazolidine are used as starting materials, the course of the reaction can be represented by the following equation:

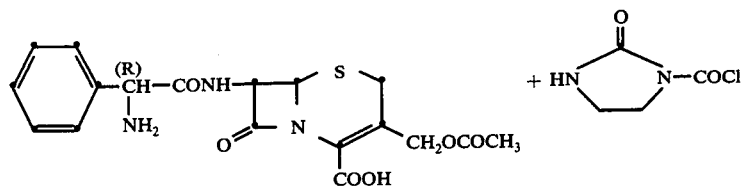

(Cephaloglycin)

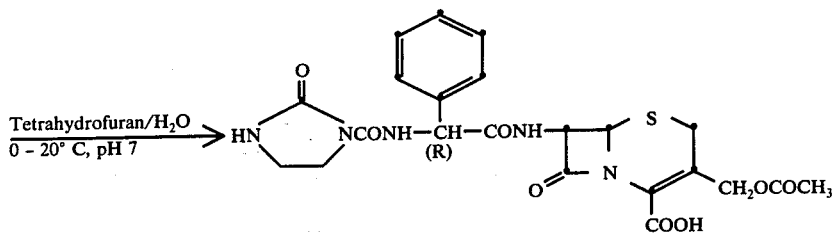

The compounds of the present invention are particularly useful for their antibacterial activity against bacteria of the family Enterobacteriaceae and Pseudomonadaceae and exhibit a higher level of activity than the known cephalosporins such as cephalexin and cephalothin which are known in the art.

The alkyl moieties of A and $R_1$ include the straight and branched chain alkyl moieties of 1 to 4 carbon atoms and, especially, 1 or 2 carbon atoms which are unsubstituted or substituted as indicated above. These include methyl, ethyl, n-propyl, i-propyl, n-butyl, i-butyl and t-butyl.

When the alkyl moieties A and $R_1$ are substituted, the substituents include fluorine, chlorine, bromine, iodine, cyano and nitro, representative examples of which include the following moieties: chloromethyl, fluoromethyl, trifluoromethyl, chlorodifluoromethyl, $\beta,\beta,\beta$-trifluoroethyl, pentafluoroethyl, cyanomethyl, $\beta$-cyanoethyl, $\gamma$-cyanopropyl, nitromethyl, $\beta$-nitroethyl and $\gamma$-nitropropyl.

The alkyl substituent of $R_2$-SO includes methyl, ethyl, n-propyl, i-propyl, n-butyl, i-butyl and t-butyl. Preferred alkyl moieties include unsubstituted methyl and ethyl, cyanomethyl and $\beta$-cyanoethyl. Preferred alkyl moieties $R_1$ include unsubstituted methyl and ethyl, cyanomethyl, cyanoethyl, trifluoromethyl, pentafluoroethyl and methylsulphonylmethyl.

The preferred aryl moieties for A and $R_1$ are phenyl and naphthyl, preferably phenyl.

The preferred monoalkylamino and dialkylamino moieties for $R_1$ include methylamino, diethylamino, dimethylamino and methylethylamino. Methylamino, ethylamino and dimethylamino are preferred.

The pyrrolidyl and piperidyl heterocycles of $R_1$ are preferably bonded to X via the ring nitrogen atom.

When X is a CO group and $R_1$ can thus also include an alkoxy moiety, the preferred alkoxy moieties include methoxy, ethoxy, n-propoxy, i-propoxy, n-butoxy, i-butoxy and t-butoxy. Methoxy is preferred.

The thienyl and furyl heterocycles of $R_1$ are preferably bonded in the 2-position.

The methyl, chloro and hydroxy moieties attached to the phenyl ring as part of substituent B can be in either the ortho, meta or para position with respect to the linking position of the phenyl ring to X. The para position is preferred.

E is preferably hydrogen or acetoxy, especially acetoxy.

Halogen W includes fluorine, chlorine, bromine and iodine, especially chlorine and bromine, and, particularly, chlorine. When W is a nitrophenoxy or dinitrophenoxy moiety, the nitro groups may be in the ortho, meta and/or para positions to the bonding position of the phenyl ring to the oxygen atom.

When W is a halogenophenoxy moiety containing 1 to 5 halogeno moieties, the halogeno moieties may be the same or different and are preferably fluorine, chlorine and bromine, particularly chlorine and/or bromine. Preferably the halophenoxy moiety contains 1 or 2 halogen atoms.

In one embodiment the invention pertains to a compound selected from the group consisting of a cephalosporin derivative of the formula:

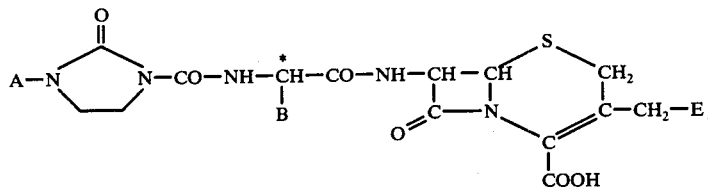

the nontoxic salts thereof and the hydrates thereof wherein the carbon atom designated * constitutes a center of chirality;

E is hydrogen, hydroxy or acetoxy;

B is phenyl, methylphenyl, chlorophenyl, hydroxyphenyl or cyclohexa-1,4-dien-1-yl; and A is (a) hydrogen; (b) alkyl of 1 to 4 carbon atoms unsubstituted or substituted by one to five substituents selected from the group consisting of halo, cyano and nitro; (c) cycloalkyl of 3 to 7 carbon atoms; (d) aryl of 6 to 10 carbon atoms unsubstituted or substituted by one to five substituents selected from the group consisting of halo, cyano, alkyl of 1 to 4 carbon atoms, alkoxy of 1 to 4 carbon atoms, and alkylsulfamyl of 1 to 4 carbon atoms; (e) carbalkoxy in which alkoxy contains 1 to 4 carbon atoms; or (f) $R_1$-X in which X is —CO— or $SO_2$—; and $R_1$ is hydrogen, alkyl of 1 to 4 carbon atoms unsubstituted or substituted by from one to five substituents selected from the group consisting of halo, cyano, nitro, and alkylsulfonyl of 1 to 5 carbon atoms, thienyl, furyl, piperidyl, pyrrolidyl, amino, alkylamino of 1 to 4 carbon atoms, dialkylamino of 1 to 4 carbon atoms in each alkyl group, or aryl of 6 to 10 carbon atoms, unsubstituted or substituted by one to five substituents selected from the group consisting of halo, cyano, alkyl of 1 to 4 carbon atoms, alkoxy of 1 to 4 carbon atoms and alkylsulfamyl of 1 to 4 carbon atoms.

In a further embodiment of the invention:

A is hydrogen; alkyl of 1 to 4 carbon atoms unsubstituted or substituted by cyano, nitro or one to five halo atoms; cycloalkyl of 3 to 7 carbon atoms; or phenyl unsubstituted or substituted by halo, cyano, methyl, ethyl, methoxy, ethoxy, methylsulfamyl or ethylsulfamyl.

In a further embodiment of the invention:

A is hydrogen; alkyl of 1 or 2 carbon atoms unsubstituted or substituted by cyano, nitro or one to three fluoro, bromo or chloro atoms; cyclopropyl; cyclobutyl; cyclopentyl; cyclohexyl; or phenyl, unsubstituted or substituted by chloro, bromo, fluoro, cyano, methyl, ethyl, methoxy, ethoxy, methylsulfamyl or ethylsulfamyl; and B is phenyl; 4-methylphenyl; 4-chlorophenyl; 4-hydroxyphenyl; or cyclohexa-1,4-dien-1-yl.

In a further embodiment of the invention:

A is carbalkoxy in which alkoxy contains 1 to 4 carbon atoms or $R_1$-X in which X is —CO— or —$SO_2$— and $R_1$ is hydrogen; alkyl of 1 to 4 carbon atoms unsubstituted or substituted by halo, cyano, nitro, alkylsulfonyl of 1 to 5 carbon atoms, or one to five halo atoms; thienyl; furyl, piperidyl, pyrrolidyl; amino; alkylamino of 1 to 4 carbon atoms; dialkylamino of 1 to 4 carbon atoms in each alkyl group; or phenyl unsubstituted or substituted by halo, cyano, methyl, ethyl, methoxy, ethoxy, methylsulfamyl or ethylsulfamyl.

In a further embodiment of the invention:

A is hydrogen; carbomethoxy; carbethoxy; or $R_1$-X in which $R_1$ is alkyl of 1 or 2 carbon atoms unsubstituted or substituted by cyano, nitro, methylsulfonyl, ethylsulfonyl, or one to three fluoro, bromo, or chloro atoms; thienyl; furyl, piperidino, pyrrolidino; amino; methylamino; ethylamino, dimethylamino; diethylamino; or phenyl, unsubstituted or substituted by chloro, fluoro, bromo, cyano, methyl, ethyl, methoxy, ethoxy, methylsulfamyl or ethylsulfamyl; and B is phenyl; 4-methylphenyl; 4-chlorophenyl; 4-hydroxyphenyl; or cyclohexa-1,4-dien-1-yl.

The salts of a compound of the present invention include the sodium, potassium, magnesium, calcium, aluminum, ammonium, mono-, di- or tri- alkylamines of 1 to 4 carbon atoms in the alkyl moiety, procaine, dibenzylamine, N,N'-dibenzylethylenediamine, N-benzyl-β-phenylethylamine, N-methylmorpholine, N-ethylmorpholine, 1-ephenamine, dehydroabietylamine, N,N'-bis-dehydroabietylethylenediamine, or N-lower alkylpiperidine.

As indicated above, the compounds of the present invention include not only the free acids but the pharmaceutically-acceptable, nontoxic salts and the various crystalline forms, including the hydrates, such as the mono-, di- and tri-hydrate forms, and the anhydrous form.

The compounds of formula II may be used in any of the crystalline forms, dehydrated forms or in the form of a pharmaceutically-acceptable, nontoxic salt salt, in which case the free acid can be recovered by reacting the salt formed with an appropriate acid. The N-silyl compounds and the easily splittable derivatives of the acid carboxyl group, such as, for example, the esters, amides and hydrazides, are additional forms of the compounds of formula II which can be used according to the process above described.

The compounds of the formula II used as starting materials are per se known. They are described, for example, in German Offenlegungsschriften 1,670,625, 1,795,188 and 1,795,292; U.S. Pat. Nos. 3,303,193, 3,352,858, 3,485,819 and 3,634,416; Japanese Patent Application 16,871/66; and British Patent No. 1,073,530.

The following compounds are representative of those of the formula II:

7-(α-amino-phenylacetamido)-3-methyl-ceph-3-em-4-carboxylic acid;

7-(α-amino-phenylacetamido)-3-hydroxymethyl-ceph-3-em-4-carboxylic acid;

7-(α-amino-phenylacetamido)-3-acetoxy-methyl-ceph-3-em-4-carboxylic acid;

7-(α-amino-4-methyl-phenylacetamido)-3-acetoxymethyl-ceph-3-em-4-carboxylic acid;

7-(α-amino-4-methylphenylacetamido)-3-methyl-ceph-3-em-4-carboxylic acid;

7-(α-amino-4-methylphenylacetamido)-3-hyroxymethyl-ceph-3-em-4-carboxylic acid;

7-(α-amino-4-chlorophenylacetamido)-3-methyl-ceph-3-em-4-carboxylic acid;

7-(α-amino-4-chlorophenylacetamido)-3-hydroxymethyl-ceph-3-em-4-carboxylic acid;

7-(α-amino-4-chlorophenylacetamido)-3-acetoxymethyl-ceph-3-em-4-carboxylic acid;

7-(α-amino-4-hydroxyphenylacetamido)-3-acetoxymethyl-ceph-3-em-4-carboxylic acid;

7-(α-amino-4-hydroxyphenylacetamido)-3-methyl-ceph-3-em-4-carboxylic acid;

7-(α-amino-4-hydroxyphenylacetamido)-3-hyroxymethyl-ceph-3-em-4-carboxylic acid;

7-(α-amino-cyclohexa-1,4-dien-1-yl-acetamido)-3-acetoxymethylmethyl-ceph-3-em-4-carboxylic acid;

7-(α-amino-cyclohexa-1,4-dien-1-yl-acetamido)-3-methyl-ceph-3-em-4-carboxylic acid; and 7-(α-amino-cyclohexa-1,4-dien-1-yl-acetamido)-3-hydroxymethyl-ceph-3-em-4-carboxylic acid.

The compounds of the formula III used as starting materials are per se known or are prepared according to procedures per se known from compounds of the formula IV (which are per se known or easily obtainable according to known procedures):

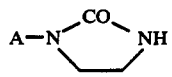 (IV)

wherein

A is as above defined, and is, in particular, phosgene. Those compounds of the formula III in which W is azido are obtained from the corresponding compounds of the formula III, in which W is halo, for example, chloro, by reaction with, for example, alkali metal azides. Those compounds of the formula III in which W is an unsubstituted or substituted phenyl radical or benzylthio radical are prepared from the compounds of the formula III in which W is halo, and the corresponding phenols or benzylmercaptan, or by reaction of compounds of the formula IV with the appropriate chlorocarbonic acid or chlorothiocarbonic acid ester.

The following compounds are representative of those of the formula III:

1-chlorocarbonyl-2-oxo-imidazolidine;
1-azidocarbonyl-2-oxo-imidazolidine;
1-phenoxycarbonyl-2-oxo-imidazolidine;
1-p-nitrophenoxycarbonyl-2-oxo-imidazolidine;
1-o-chlorophenoxycarbOnyl-2-oxo-imidazolidine;
1-chlorocarbonyl-2-oxo-3-methyl-imidazolidine;
1-azidocarbonyl-2-oxo-3-methyl-imidazolidine;
1-chlorocarbonyl-2-oxo-3-ethyl-imidazolidine;
1-azidocarbonyl-2-oxo-3-ethyl-imidazolidine;
1-chlorocarbonyl-2-oxo-3-phenyl-imidazolidine;
1-azidocarbonyl-2-oxo-3-phenyl-imidazolidine;
1-chlorocarbonyl-2-oxo-3-methylsulphonyl-imidazolidine;
1-chlorocarbonyl-2-oxo-3-cyanomethylsulphonyl-imidazolidine;
1-chlorocarbonyl-2-oxo-3-$\beta$-cyanoethylsulphonyl-imidazolidine;
1-chlorocarbonyl-2-oxo-3-trifluoromethylsulphonyl-imidazolidine;
1-chlorocarbonyl-2-oxo-3-methylaminosulphonyl-imidazolidine;
1-chlorocarbonyl-2-oxo-3-phenylsulphonyl-imidazolidine;
1-chlorocarbonyl-2-oxo-3-thienyl(2)sulphonyl-imidazolidine;
1-chlorocarbonyl-2-oxo-3-furyl(2)sulphonyl-imidazolidine;
1-chlorocarbonyl-2-oxo-3-formyl-imidazolidine;
1-chlorocarbonyl-2-oxo-3-methylcarbonyl-imidazolidine;
1-chlorocarbonyl-2-oxo-3-ethylcarbonyl-imidazolidine;
1-chlorocarbonyl-2-oxo-3-trifluoromethylcarbonyl-imidazolidine;
1-chlorocarbonyl-2-oxo-3-pentafluoroethylcarbonyl-imidazolidine;
1-chlorocarbonyl-2-oxo-3-phenylcarbonyl-imidazolidine;
1-chlorocarbonyl-2-oxo-3-thienylcarbonyl-imidazolidine;
1-chlorocarbonyl-2-oxo-3-furylcarbonyl-imidazolidine;
1-chlorocarbonyl-2-oxo-3-cyanomethylcarbonyl-imidazolidine;
1-chlorocarbonyl-2-oxo-3-$\beta$-cyanoethylcarbonyl-imidazolidine; and
1-chlorocarbonyl-2-oxo-3-methylsulphonyl-methylsulphonyl-imidazolidine.

Suitable diluents for the process of the present invention are both mixtures of water with water-miscible, organic solvents, such as ketones, for example, acetone and methyl ethyl ketone; ethers, for example, tetrahydrofurane and dioxane; lower alkylnitriles, for example, acetonitrile; dimethylformamide; alkyl alcohols, for example, isopropanol; and/or dimethylsulphoxide; and these organic solvents (individually or as mixtures) without added water. If it is possible to measure the pH during the reaction according to the present invention because of the presence of water, the pH value of the reaction is preferably kept at between 6.5 and 7.5 by added bases or by using buffer mixtures. However, the reaction according to the present invention can also be carried out in a different pH range, for example, between 4.5 and 9.0, or at pH 2.0 to 4.5. Furthermore, it is possible to carry out the reaction in water-immiscible solvents, such as halogenated hydrocarbons, for example, chloroform or methylene chloride, with addition of organic amines, preferably triethylamine, diethylamine or N-ethylpiperidine. The reaction can also be carried out in a mixture of water and a water-immiscible organic solvent, such as, for example, ether (diethyl ether); halogenated hydrocarbons, for example, chloroform and also methylene chloride; carbon disulphide; water-immiscible ketones, for example, isobutyl methyl ketone; esters, for example, ethyl acetate; or hydrocarbons; for example, benzene; in which case it is advisable to stir the mixture vigorously and keep the pH value between about 4.5 and 9.0, or, for example, 2.0 and 3.0, by adding bases or using buffer solutions. However, the reaction can also be carried out in water alone; that is to say, in the absence of organic solvents, in the presence of an organic or inorganic base or with the addition of buffer substances.

Organic bases suitable to be added according to the process of the present invention include tertiary aliphatic or aromatic amines, for example, pyridine; or lower trialkylamines, for example, triethylamine; or secondary aliphatic or aromatic amines, which, because of steric hindrance, are difficult to acylate, for example, dicyclohexylamine.

Inorganic bases which can be used are, above all, alkali metal hydroxides and alkaline earth metal hydroxides; for example, sodium hydroxide or potassium hydroxide and calcium hydroxide.

The amount of the bases used is determined, for example, by the desired maintenance of a particular pH (compare the comments above). If a pH measurement and adjustment is not carried out or is not possible, or not meaningful, because of the absence of sufficient amounts of water in the diluent, preferably about 1 to 5, especially about 2, mol equivalents of base are added.

Examples of buffer mixtures which can be used are phosphate buffers (sodium phosphate/phosphoric acid), acetate buffers (sodium acetate/acetic acid) and citrate buffers (sodium citrate/citric acid), and the mixing ratios required to maintain the desired pH values can easily be determined.

The reaction temperature can be varied within a substantial range. In general, the reaction is carried out at between $-20°$ C and about $+50°$ C, preferably between $0°$ C and $+20°$ C. As in the case of most chemical reactions, higher or lower temperatures than those specified in the examples can be used.

The reaction can be carried out under atmospheric pressure but also under reduced or elevated pressure. In general, it is carried out at atmospheric pressure.

In carrying out the process according to the present invention, the reactants can be reacted with one another in, for example, equimolar amounts. However, it can also be advisable to use one of the two reactants in excess in order to facilitate the purification, or preparation in a pure form, of the desired cephalosporin and to increase the yield. The amounts of the reactants of the formulae II and III can be varied greatly without adverse consequences. For example, the reactants of the formula II can be employed in an excess of 0.1 to 0.3 mol equivalent and less decomposition of the reactants of the formula III in an aqueous solvent mixture can thereby be achieved. The excess of the reactants of the formula II can easily be removed when working up the reaction mixture, because of the good solubility in aqueous mineral acids. On the other hand, it is, however, also possible, with advantage, to employ the reactants of the formula III in an excess of, for example, 0.1 to 1.0 mol equivalent. As a result of this, the reactants of the formula III are utilized better and the decomposition of the reactants of the formula III, which takes place as a side reaction in aqueous solvents, is compensated for. Since the compounds of the formula III added in excess rapidly change, in water, into neutral nitrogen-containing heterocyclic compounds, which can easily be removed, the purity of the cephalosporins is hardly impaired thereby.

The working up of the reaction batches to prepare the cephalosporins of the formula I and their salts and the purification of the new compounds is throughout effected in the manner per se known from cephalosporin chemistry. For example, the free acids of the formula I can be prepared by acidifying a solution of the salts, for example, of the sodium salts, with an inorganic or organic acid, for example, with dilute hydrochloric acid or acetic acid. The free acids of the formula I can be converted in the usual manner into the salts with nontoxic bases, for example, by adding the base in question to a solution of the acids of the formula I in ether. Other methods for effecting interconversion of the free acid and the salts are known in the art.

The following compounds are representative of those of the present invention:

7-{D-α-[(2-Oxo-imidazolidin-1-yl)-carbonylamino]-phenylacetamido}-3-acetoxymethyl-ceph-3-em-4-carboxylic acid

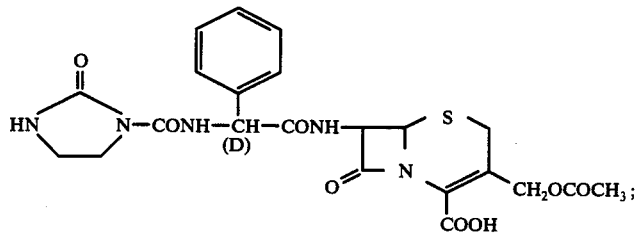

7-{D-α-[(2-Oxo-imidazolidin-1-yl)-carbonylamino]-phenylacetamido}-3-methyl-ceph-3-em-4-carboxylic acid.

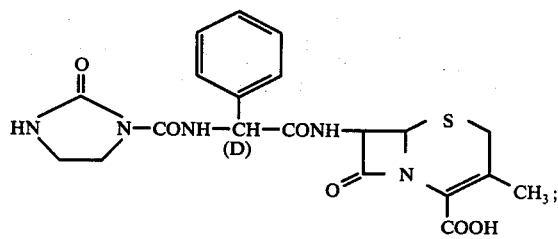

7-{D-α-[(2-Oxo-3-methyl-imidazolidin-1-yl)-carbonylamino]-phenylacetamido}-3-acetoxymethyl-ceph-3-em-4-carboxylic acid

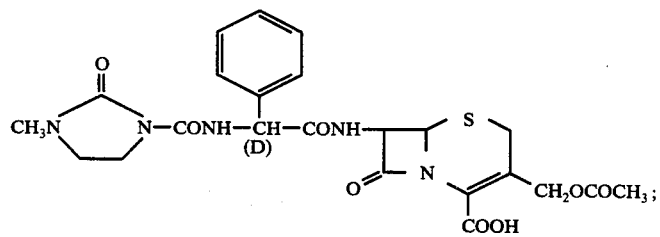

7-{D-α-[(2-Oxo-3-ethyl-imidazolidin-1-yl)-carbonylamino]-phenylacetamido}-3-acetoxymethyl-ceph-3-em-4-carboxylic acid.

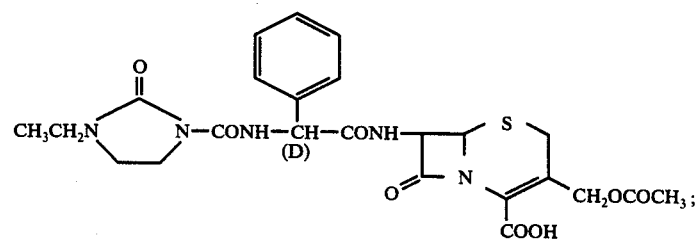

11

7-{D-α-[(2-Oxo-3-mesyl-imidazolidin-1-yl)-carbonylamino]-phenylacetamido}-3-acetoxymethyl-ceph-3-em-4-carboxylic acid

12

7-{D-α-[(2-Oxo-3-phenylsulphonyl-imidazolidin-1-yl)-carbonylamino]-phenylacetamido}-3-methyl-ceph-3-em-4-carboxylic acid.

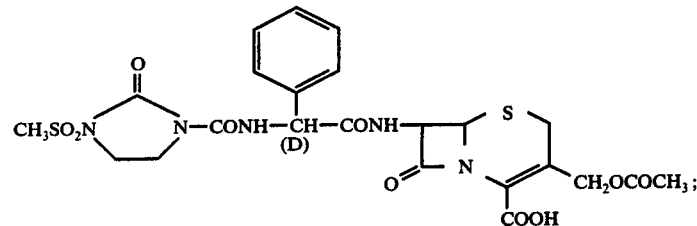

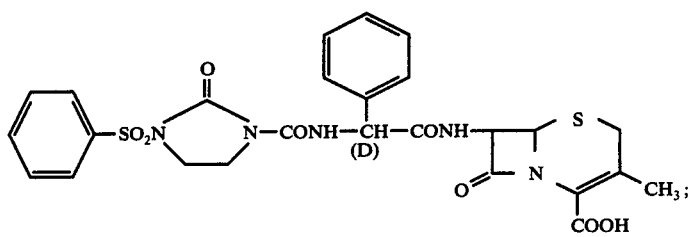

7-{D-α-[(2-Oxo-3-methylaminosulphonyl-imidazolidin-1-yl)-carbonylamino]-phenylacetamido}-3-acetoxymethyl-ceph-3-em-4-carboxylic acid 7-{D-α-[(2-Oxo-3-thienyl-(2)-sulphonyl-imidazolidin-1-yl)-carbonylamino]-phenylacetamido}-3-acetoxymethyl-ceph-3-em-4-carboxylic acid

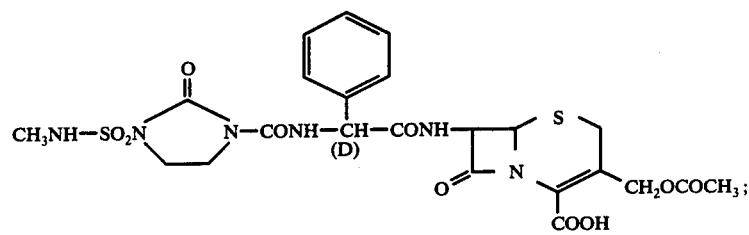

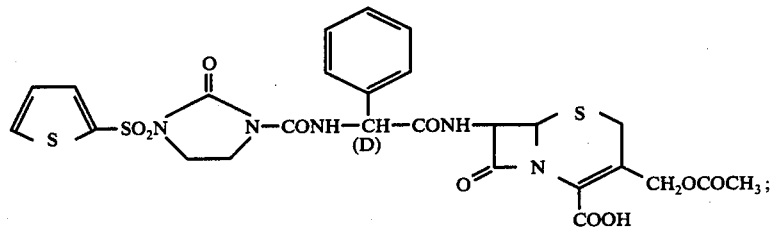

7-{D-α-[(2-Oxo-3-phenylsulphonyl-imidazolidin-1-yl)-carbonylamino]-phenylacetamido}-3-acetoxymethyl-ceph-3-em-4-carboxylic acid 7-{D-α-[(2-Oxo-3-formyl-imidazolidin-1-yl)-carbonylamino]-phenylacetamido}-3-acetoxymethyl-ceph-3-em-4-carboxylic acid.

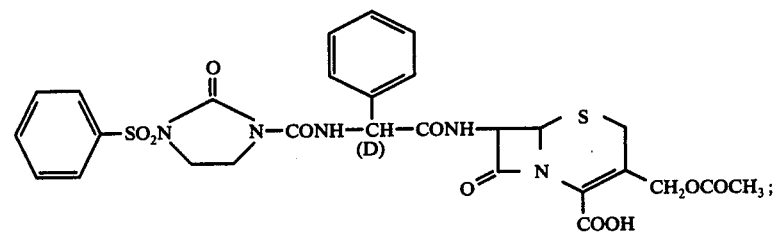

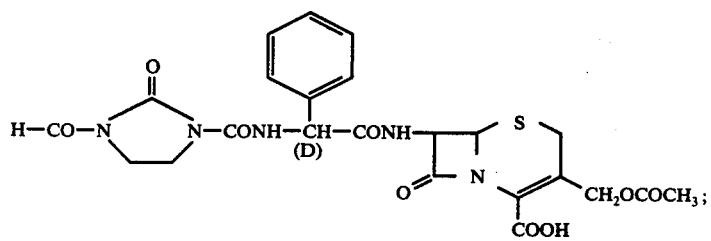

7-{D-α-[(2-Oxo-3-acetyl-imidazolidin-1-yl)-carbonylamino]-phenylacetamido}-3-acetoxymethyl-ceph-3-em-4-carboxylic acid 7-{D-α-[(2-Oxo-3-furoyl(2)-imidazolidin-1-yl)-carbonylamino]-phenylacetamido}-3-acetoxymethyl-ceph-3-em-4-carboxylic acid.

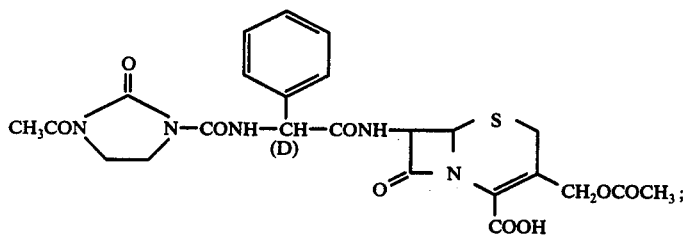

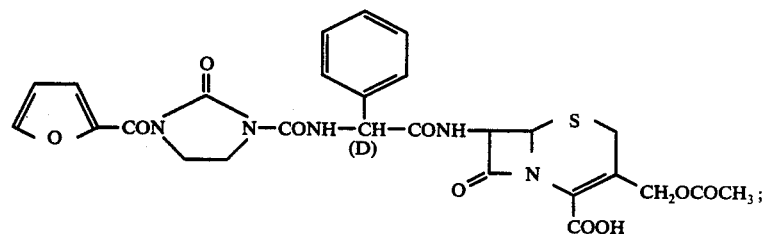

7-{D-α-[(2-Oxo-3-benzoyl-imidazolidin-1-yl)-carbonylamino]-phenylacetamido}-3-acetoxymethyl-ceph-3-em-4-carboxylic acid 7-{D-α-[(2-Oxo-3-thienyl(2)-carbonyl-imidazolidin-1-yl)-carbonylamino]-phenylacetamido}-3-acetoxymethyl-ceph-3-em-4-carboxylic acid

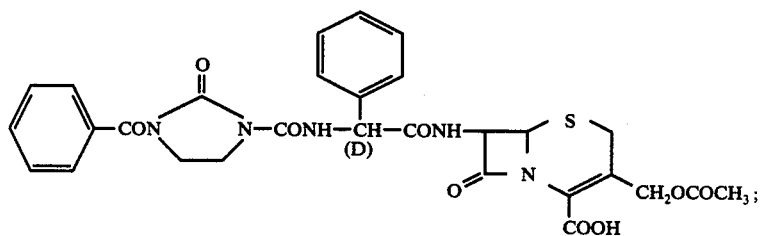

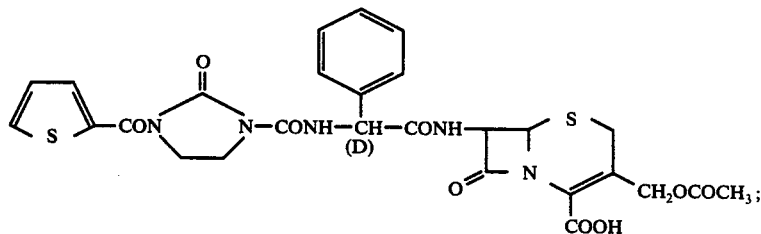

7-{D-α-[(2-Oxo-3-(mesyl)-mesyl-imidazolidin-1-yl)-carbonylamino]-phenylacetamido}-3-acetoxymethyl-ceph-3-em-4-carboxylic acid

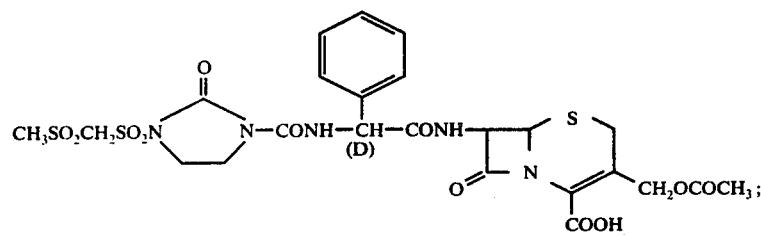

7-{D-α-[(2-Oxo-3-cyanoacetyl-imidazolidin-1-yl)-carbonylamino]-phenylacetamido}-3-acetoxymethyl-ceph-3-em-4-carboxylic acid 7-{D-α-[(2-Oxo-3-cyanomethylsulphonyl-imidazolidin-1-yl)-carbonylamino]-phenylacetamido}-3-acetoxymethyl-ceph-3-em-4-carboxylic acid

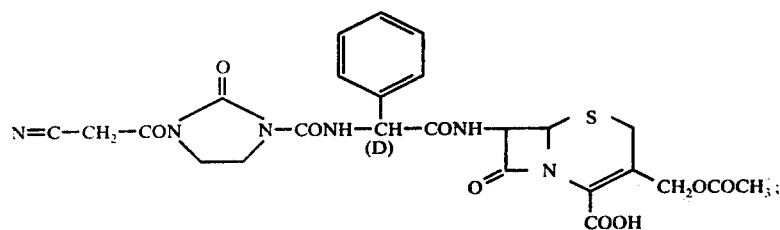

7-{D-α-[(2-Oxo-3-β-cyanopropionyl-imidazolidin-1-yl)-carbonylamino]-phenylacetamido}-3-acetoxymethyl-ceph-3-em-4-carboxylic acid 7-{D-α-[(2-Oxo-3-trifluoroacetyl-imidazolidin-1-yl)-carbonylamino]-phenylacetamido}-3-acetoxymethyl-ceph-3-em-4-carboxylic acid

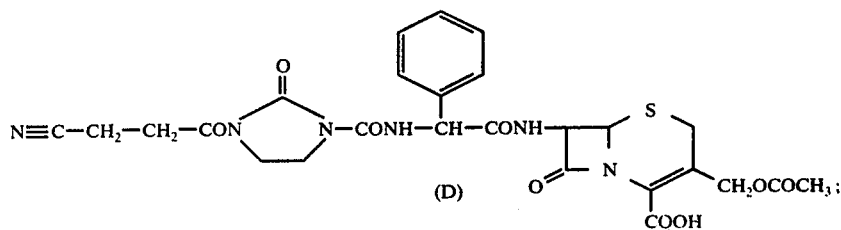

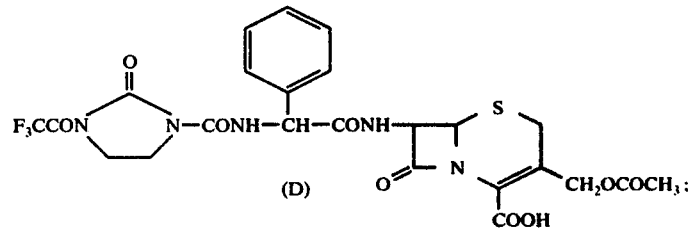

7-{D-α-[(2-Oxo-3-pentafluoropropionyl-imidazolidin-1-yl)-carbonylamino]-phenylacetamido}-3-acetoxymethyl-ceph-3-em-4-carboxylic acid

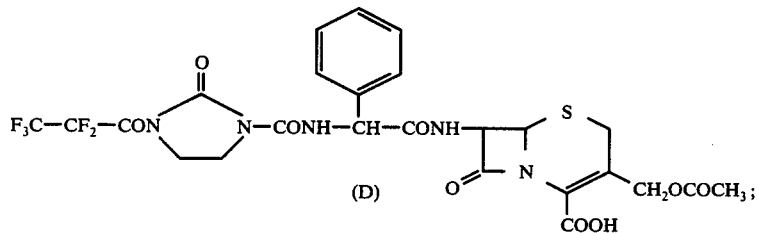

7-{D-α-[(2-Oxo-3-trifluoromethylsulphonyl-imidazolidin-1-yl)-carbonylamino]-phenylacetamido}-3-acetoxymethyl-ceph-3-em-4-carboxylic acid 7-{D-α-[(2-oxo-3-sulphamyl-imidazolidin-1-yl)-carbonylamino]-phenylacetamido}-3-acetoxymethyl-ceph-3-em-4-carboxylic acid

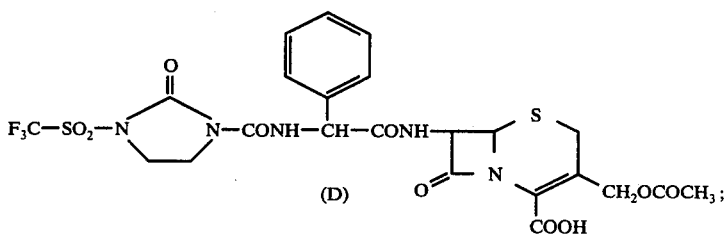

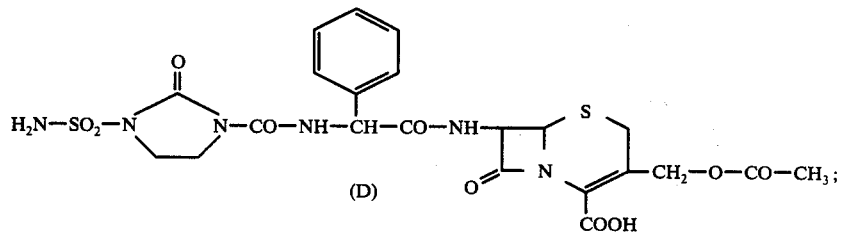

7-{D-α-[(2-Oxo-3-benzoyl-imidazolidin-1-yl)-carbonylamino]-phenylacetamido}-3-methyl-ceph-3-em-4-carboxylic acid 7-{D-α-[(2-oxo-3-phenyl-imidazolidin-1-yl)-carbonylamino]-phenylacetamido}-3-acetoxymethyl-ceph-3-em-4-carboxylic acid

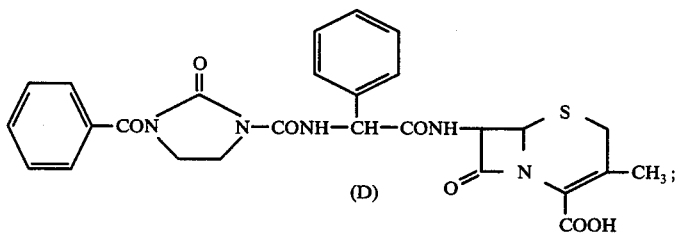

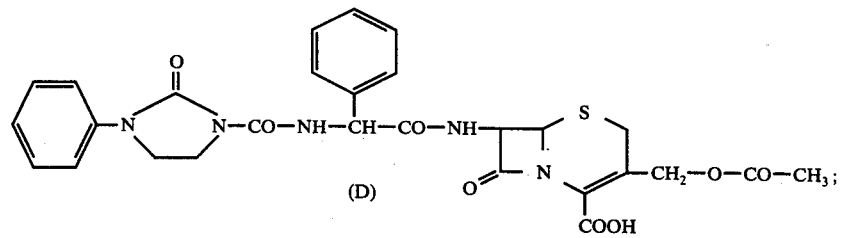

7-{D-α[(2-oxo-3-phenyl-imidazolidin-1-yl)-carbonylamino]-phenylacetamido}-3-methyl-ceph-3-em-4-carboxylic acid

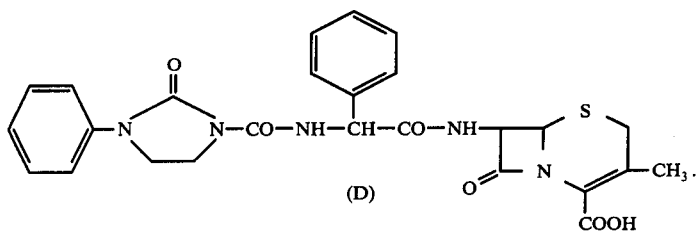

(D)

The compounds of the present invention exhibit a low toxicity, are well tolerated, and exhibit a strong antimicrobial, and, particularly, antibacterial, activity. They are thus particularly useful for their antimicrobial and antibacterial activity and for preserving inorganic and organic materials such as polymers, lubricants, dyestuffs, fibers, leather, paper, timber, foodstuffs and water.

Compounds of the present invention are useful for treating and preventing infections caused by the following pathogens:

Micrococcaceae, such as Staphylococci, for example *Staphylococcus aureus, Staph. epidermidis, Staph. aerogenes* and *Gaffkya tetragena* (Staph. = Staphylococcus);

Lactobacteriaceae, such as Streptococci, for example *Streptococcus pyogenes*, α- and β-haemolysing Streptococci, non-(-)-haemolysing Streptococci, *Str. viridans, Str. faecalis* (Enterococci), *Str. Agalactiae, Str. lactis, Str. equi, Str. anaerobis* and *Diplococcus pneumoniae* (Pneumococci) (Str. = Streptococcus), Neisseriaceae, such as Neisseria, for example *Neisseria gonorrhoeae* (Gonococci), *N. meningitidis* (Meningococci), *N. catarrhalis* and *N. flava* (N. = Neisseria);

Corynebacteriaceae, such as Corynbacteria, for example *Corynebacterium diphtheriae, C. pyogenes, C. diphtheroides, C. acnes, C. parvum, C. bovis, C. renale, C. ovis* and *C. murisepticum*, Listeria bacteria, for example *Listeria* bacteria, for example *Listeria monocytogenes*, Erysipelothrix bacteria, for example *Erysipelothrix insidiosa*, and Kurthia bacteria, for example *Kurthia zopfii* (C. = Corynebacterium);

Mycobacteriaceae, such as pathogens of mycobacterioses, for example *Mycobacterium tuberculosis, M. bovis, M. avium*, so-called a typical mycobacteria of the Runyon groups I, II, III and IV, and *M. leprae* (M. = Mycobacterium);

Enterobacteriaceae, such as *Escherichiae* bacteria of the *coli* group, Escherichia bacteria, for example *Escherichia coli*, Enterobacter bacteria, for example *E. aerogenes* and *E. cloacae*, Klebsiella bacteria, for example *K. pneumoniae* and *K. ozaenae*, Erwiniae, for example Erwinia spec. and Serratia, for example *Serratia marcescens* (E. = Enterobacter) (K. = Klebsiella), Proteae bacteria of the Proteus group, Proteus, for example *Proteus vulgaris, Pr. morganii, Pr. rettgeri* and *Pr. mirabilis* (Pr. = Proteus), Providencia, for example Providencia sp., Salmonelleae, Salmonella bacteria, for example *Salmonella paratyphi* A and B, *S. typhi, S. enteritidis, S. cholerae suis* and *S. typhimurium* (S. = Salmonella), and Shigella bacteria, for example *Shigella dysenteriae, Sh. ambigua, Sh. flexneri, Sh. boydii* and *Sh. sonnei* (Sh. = Shigella);

Pseudomonadaceae, such as pseudomonas bacteria, for example *Pseudomonas aeruginosa* and *Ps. Pseudomallei* (Ps. = Pseudomonas), and Aeromonas bacteria, for example *Aeromonas liquefaciens* and *A. hydrophila* (A. = Aeromonas);

Spirillaceae, such as Vibrio bacteria, for example *Vibrio cholerae, V. Proteus* and *V. fetus* (V. = Vibrio), and Spirillum bacteria, for example *Spirillum minus*;

Parvobacteriaceae or Brucellaceae, such as Pasteurella bacteria, for example *Pasteurella multocida, Past. pestis* (Yersinia), *Past. pseudotuberculosis* and *Past. tularensis* (Past. = Pasteurella), Burcella bacteria, for example *Brucella abortus, Br. melitensis* and *Br. suis* (Br. = Brucella), Haemophilus bacteria, for example *Haemophilus influenzae, H. ducreyi, H. suis, H. canis* and *H. aegypitcus* (H. = Haemophilus), Bordetella bacteria, for example *Bordetella pertussis* and *B. bronchiseptica* (B. = Bordetella), and Moraxella bacteria, for example *Moraxella lacunata*;

Bacterioidacea, such as Bacterioides bacteria, for example *Bacteroides fragilis* and *B. serpens* (B. = Bacteroides), Fusiform bacteria, for example *Fusobacterium fusiforme*, and Sphaerophorus bacteria, for example *Sphaerophorus necrophorus, Sph. necroticus* and *Sph. pyrogenes* (Sph. = Sphaerophorus);

Acromobacteriaceae, such as *Flavobacterium alcaligensis faecalis*, and Achromobacter, for example *Achromobacter anitratus*;

Bacillaceae, such as aerobic spore-forming organisms, for example *Bacillus anthracis, B. subtilis* and *B. cereus* (B. = Bacillus), and anaerobic spore-forming chlostridia, for example *Clostridium perfringens, Cl. septicium, Cl. oedematiens, Cl. histolyticum, Cl. tetani* and *Cl. botulinum* (Cl. = Clostridium);

Spirochaetaceae, such as Borrelia bacteria, for example *Borrelia recurrentia* and *B. vincentii* (B. = Borrelia), Treponema bacteria, for example *Treponema pallidum, Tr. pertinue* and *Tr. carateum* (Tr. = Treponema), Leptospira bacteria, for example *Leptospira interrogans, Leptospira icterohaemorrhagiae, L. canicola, L. grippotyphosa, L. pomona, L. mitis* and *L. bovis* (L. = Leptospira);

The following may be mentioned as examples of illnesses which can be prevented, ameliorated and/or healed by the active compounds according to the present invention: illnesses of the respiratory tracts and of the throat; otitis; pharyngitis; pneumonia; peritonitis; pyelonephritis; cystitis; endocarditis; systemic infections; bronchitis; arthritis.

The pharmaceutical compositions of the present invention contain a major or minor amount, e.g. 0.1% to 99.5%, preferably 0.5% to 95%, of active ingredient as above defined in combination with a pharmaceutically acceptable, nontoxic, inert diluent or carrier, the carrier comprising one or more solid, semi-solid or liquid diluent, filler and formulation adjuvant which is nontoxic, inert and pharmaceutically-acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or fourth of a single dose. A single does preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be from 6 to 800, preferably 15 to 300, mg/kg of body weight per day. In some instances, a sufficient therapeutic effect can be obtained at a lower dose, while in others, a larger dose will be required.

Oral administration can be effected utilizing solid and liquid dosage unit forms such as powders, tablets, dragees, capsules, granulates suspensions, solutions and the like.

Powders are prepared by comminuting the compound to a suitable fine size and mixing with a similarly comminuted pharmaceutical carrier such as an edible carbohydrate as, for example, starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example, by preparing a powder mixture, granulating or slugging, adding a lubricant and disintegrant and pressing into tablets. A powder mixture is prepared by mixing the compound, suitably cominuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phophate. The powder mixture can be granulted by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared by prolong or sustain the release, as, for example, by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection, such as an aqueous or oleaginous medium, and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble, or insoluble solids such as polyethylene glycol, cocoa butter, higher esters, as, for example, myristyl palmitate, or mixtures thereof.

Topical administration can be effected utilizing solid dosage unit forms such as powders or liquid or semi-liquid dosage unit forms such as solutions, suspensions, ointments, pastes, creams and gels. The powders are formulated utilizing such carriers as talc, bentonite, silicic acid, polyamide powder and the like. Liquid and semi-liquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellents such as the chlorofluorohydrocarbons.

The preferred daily dose is from 6 to 800, preferably 15 to 300, mg/kg, preferably 15 to 300 mg/kg of active agent. This may be broken up into smaller dosages of from 2 to 300 mg/kg, preferably 5 to 100 mg/kg.

While the routes of administration include oral, parenteral (i.e., intramuscular, intraperitoneal, and intravenous), rectal, and topical, parenteral administration is particularly preferred.

The preferred pharmaceutical compositions are therefore those in a form suitable for parenteral administration such as solutions and emulsions.

The compounds of the present invention may also be used as a feedstuff additive in the treatment of non-human animals, such as ruminants. The present invention therefore includes a medicated fodder incorporating a compound according to the present invention and a nutritious material. Examples of typical nutritious materials are oil cake grains (such as barley), fish meal, soya bean meal, extracted sugar beets, silage hay and skimmed milk.

The new cephalosporins are distinguished by powerful antibacterial effects which have been tested in vivo and in vitro, and by oral resorbability.

The cephalosporins according to the present invention can be combined with aminoglycoside antibiotics such as Gentamicin, Sisomicin, Kanamicin, Amikacin or Tobramicin, to broaden the spectrum of action or to boost the action.

The activity of the compounds according to the present invention can, by way of example, be demonstrated by the following in vitro and in vivo experiment:

a. In vitro experiment

The cephalosporins of Examples 3, 6 and 7, which can be regarded as typical representatives of the compounds according to the present invention, were diluted to a strength of 100 μg/ml with Muller-Hinton nutrient broth, with addition of 0.1% by weight of glucose. The nutrient solution in each case contained $1 \times 10^5$ to $2 \times 10^5$ bacteria per milliliter. The test tubes containing this mixture were incubated for 24 hours in each case and the degree of turbidity was then determined. Freedom from turbidity indicates that the compounds were active. At a dosage of 100 μg/ml, the following bacteria cultures were free from turbidity (sp. = species): *Klebsiella pneumoniae; Enterobacter aerogenes* sp.; *Providencia; Serratia marcescens; Escherichia coli* BE; *Salmonella* sp.; *Shigella* sp.; *Proteus*, indole negative and indole positive sp.; *pasteurella pseudotuberculosis; Brucella* sp.; *Haemophilis influenzae; Bordetella bronchiseptica; Staphylococcus aureus* 133; *Neisseria catarrhalis* sp.; *Diplococcus pneumoniae* sp.; *Streptococcus pyogenes* W.; *Enterococcus* sp.; *Lactobacillus* sp.; *Corynebacterium diphtheria* gravis; *Corynebacterium pyogenes* M.

b. In vivo experiment

Table 1, which follows, shows the action of one of the cephalosporins according to the present invention, which can be regarded as typical of the compounds according to the present invention, against a series of bacteria in animal experiments with white mice. The white mice of strain $CF_1$ were infected intraperitoneally with the species of bacteria indicated.

Table 1

| Animal Experiments With White Mice | |
|---|---|
| Determination of the ED $_{50}$ after 24 hours | |
| Germ | Dose in mg of the cephalosporin from Example 6 per kg of body weight (administered subcutaneously) |
| *Escherichia coli* C 165 | 1 × 200 |
| *Staphylococcus aureus* 133 | 1 × 10 |
| *Klebsiella* | 1 × 150 |

Table 1-continued

| Animal Experiments With White Mice | |
|---|---|
| Therapy: 1 administration 30 minutes after infection. | |
| The ED $_{50}$ is the dose at which 50% of the infected animals still survive after 24 hours. | |

Explanation of abbreviations used:

| Parts by wt. | = parts by weight |
|---|---|
| Parts by vol. | = parts by volume |
| Mins. | = minutes |
| Hr. | = hour |
| Hrs. | = hours |
| M.p. | = melting point |
| Dec.p. | =0 decomposition point |
| i.v. | = in vacuo |
| Ethyl acetate | = ethyl acetate |
| Ether | = diethyl ether |
| DMSO | = dimethylsulphoxide |
| Mesyl | = methylsulphonyl |

All yields quoted in % are % of theory.
All temperatures are given in ° C.

The 7-(α-amino-phenylacetamido)-3-methyl-ceph-3-em-4-carboxylic acid used in the examples which follow contained about 5% of water by anhydrous 7-(α-amino-phenylacetamido)-3-methyl-ceph-3-em-4-carboxylic acid can also be used equally well.

The 7-(α-amino-phenylacetamido)-3-acetoxymethyl-ceph-3-em-4-carboxylic acid used in the examples which follow contained 8% of water but anhydrous 7-(α-amino-phenylacetamido)-3-acetoxymethyl-ceph-3-em-4-carboxylic acid can also be used equally well.

"Cefalexin" denotes the 7-(α-amino-phenylacetamido)-3-methyl-ceph-3-em-4-carboxylic acid with the D = R-configuration in the side chain and "cephaloglycine" denotes the 7-(α-amino-phenylacetamido)-3-acetoxymethyl-ceph-3-em-4-carboxylic acid with the D = R-configuration in the side chain.

Unless stated otherwise in the examples, the NMR spectra of the cephalosporins were recorded in $CD_3OD$ solution. The codes in parentheses denote the following:

| s = singlet | m = multiplet |
|---|---|
| d = doublet | AB = AB system |
| t = triplet | AX = AX system |
| q = quartet | $A_2B_2$ = $A_2B_2$ system |

The IR spectra of the cephalosporins were recorded in Nujol suspension.

The β-lactam content of the cephalosporins was determined from the extinction of the β-lactamcarbonyl band of the IR spectrum and from the NMR spectrum.

The following nonlimitative examples more particularly illustrate the present invention:

EXAMPLE 1

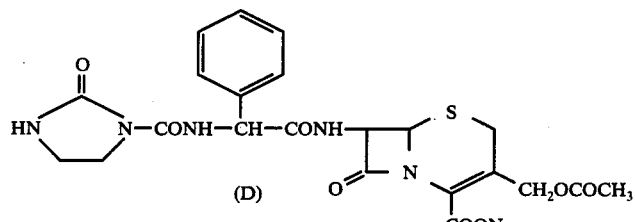

A)

A suspension of 1.3 parts by wt. of cephaloglycine dihydrate in 15 parts by vol. of 80% strength aqueous tetrahydrofurane was adjusted to pH 7.5 with triethylamine and 0.51 part by wt. of 1-chlorocarbonyl-2-oxo-imidazolidine was added in portions over the course of 10 mins. at temperatures between 10° C and 20° C, while keeping the pH at 7–8 with triethylamine. The mixture was stirred further unitl it was no longer necessary to add triethylamine to maintain a pH of 7–8. 20 parts by vol. of water were now added, the tetrahydrofurane was stripped off at room temperature on a rotary evaporator and the aqueous solution was extracted once with ethyl acetate, and filtered off. It was covered with 20 parts by vol. of ethyl acetate and acidified with 2 N HCl to pH = 2 while cooling with ice, whereupon the free acid of the cephalosporin, which is sparingly soluble in water and ethyl acetate, separated out as a crystalline precipitate. It was filtered off and washed with ethyl acetate. The product was briefly dried on a rotary evaporator and then dissolved in 5 parts by vol. of dimethylacetamide, and 3 parts by vol. of a one-molar solution of sodium 2-ethylhexanoate in ether containing a little methanol were added. The solution was now stirred into 30 parts by vol. of ether-methanol mixture (volume ratio 10:1) while cooling with ice. The product was allowed to settle out, the solvent was decanted off, and the product was suspended in ether and filtered under suction until dry. It was then dried in a vacuum desiccator over $P_2O_5$ and paraffine chips for 24 hrs.

Yield of sodium 7-{D-α-[(2-oxo-imidazolidin-1-yl)carbonylamino]-phenylacetamido}-3-acetoxymethyl-ceph-3-em-4-carboxylate: 80%.

IR bands at 3,250, 3,060, 1,765, 1,723, 1,652, 1,607 1,540, 1,274, 1,235, and 1,032 $cm^{-1}$.

NMR signals at $\tau$ = 2.55 (s, 5H), 4.27 + 4.95 (AX, 1H + 1H), 4.5 (s, 1H), 5.2 (s, 2H), 6.05–6.8 (AX, 4H), 6.5 + 6.8 (AB, 2H) and 7.9 ppm (s, 3H) (in $D_2O$).

The electropherogram showed only one spot with antibiotic activity against B. subtilis, Escherichia coli and Pseudomonas aeruginosa.

M.p. = 153° C after recrystallization from acetone-pentane.

Calculated: C 32.3, H 3.4, N 18.8, Cl 23.9, Found: C 32.3, H (4.5), N 18.7, Cl 23.9.

NMR signals at $\tau$ = 5.7 to 6.1 (2H) and 6.3 to 6.7 (2H), (acetone-$d_6$ as the solvent), symmetrical $A_2B_2$ system.

IR bands at 3,230, 1,790, 1,700, 1,270 and 1,150 $cm^{-1}$.

EXAMPLE 2

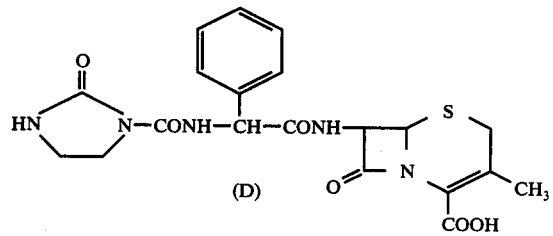

7-{D-α-[(2-Oxo-imidazolidin-1-yl)-carbonylamino]-phenylacetamido}-3-methyl-ceph-3-em-4-carboxylic acid was prepared, in the form of the crystalline free cephalosporin acid, in the manner described in Example 1 from 1.83 parts by wt. of cephalexin monohydrate and 0.82 part by wt. of 1-chlorocarbonyl-2-oxo-imidazolidine.

Yield: 86%.

IR bands at 3,335, 3,270, 3,040, 1,782, 1,724, 1,663, 1,530, 1,310, and 1,240 $cm^{-1}$.

NMR signals at = 0.6 (d, 1H), 0.8 (d, 1H), 2.3 (s, 1H), 2.6 (s, 5H), 4.0–4.4 (m, 2H), 5.0 (q, 1H), 5.9–6.9 (m, 6H) and 7.9 ppm (3H) (in DMSO-$d_6$).

The electropherogram shows only one spot with antibiotic activity.

EXAMPLE 3

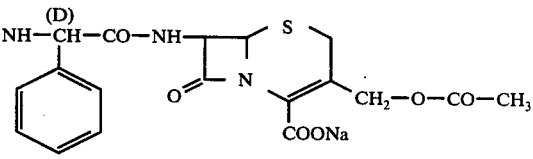

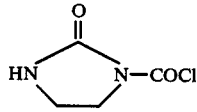

4 parts by wt. of phosgene in 10 parts by vol. of absolute tetrahydrofurane were added dropwise over the course of 15 mins. to a vigorously stirred solution of 3.5 parts by wt. of imidazolidinone-(2) (prepared according to Fischer and Koch, Ann. 232, page 224 (1886)) in 50 parts by vol. of absolute tetrahydrofurane. The reaction mixture was then stirred for 3 hours at 10° C and thereafter a stream of dry air was passed through it in order to blow out the hydrochloric acid formed, and remnants of phsogene. The mixture was now evaporated to dryness on a rotary evaporator in vacuo and the solid residue was dried over concentrated sulphuric acid and at about 12 mm Hg.

Yield: 93% of 1-chlorocarbonyl-2-oxo-imidazolidine.

2.2 parts by wt. of cephaloglycine were dissolved in 30 parts by vol. of 80% strength aqueous tetrahydrofurane by adding the amount of triethylamine just required to effect solution. 0.8 part by wt. of 1-chlorocarbonyl-2-oxo-3-methylimidazolidine was then introduced at 20° C, while stirring. In the course thereof, and subsequently, the pH was kept at 7.0 by appropriate addition of triethylamine. Stirring was continued until no further triethylamine had to be added to maintain the pH of 7.0 (approx. 1 hr.). The mixture was then diluted with an equal volume of water, the pH was adjusted to 6.5, the tetrahydrofurane was removed in vacuo, the aqueous solution which remained was covered with a mixture of ether and ethyl acetate (1:1) and acidified to pH 2 while stirring and cooling gently, the organic phase was separated off, washed with water and dried over magnesium sulphate, and the sodium salt of the cephalosporin was precipitated by means of an approximately 1-molar sodium 2-ethyl-hexanoate solution in ether containing methanol. The sodium salt separated out as a gel-like but filtrable precipitate. After washing with ether, it was dried in a desiccator.

Yield: 2.1 parts by wt. of sodium 7-{D-α-[(3-methyl-2-oxo-imidazolidin-1-yl)-carbonylamino]-phenylacetamido}-3-acetoxymethyl-ceph-3-em-4-carboxylate.

β-Lactam content: about 75%.

IR bands in the carbonyl region 1,780, 1,720, 1,650, 1,610 and 1,540 cm$^{-1}$ (in Nujol).

NMR signals at τ = 2.4–2.8 (5H); 4.15–4.35 (1H); 4.9–5.2 (4H); 6.2–6.8 (6H); 7.2 (3H); and 7.95 ppm (3H).

1-Chlorocarbonyl-2-oxo-3-methyl-imidazolidine used as the starting compound, was prepared from 1-methyl-2-oxo-imidazolidine and phosgene in tetrahydrofurane. Melting point: 94° C–95° C.

EXAMPLE 4

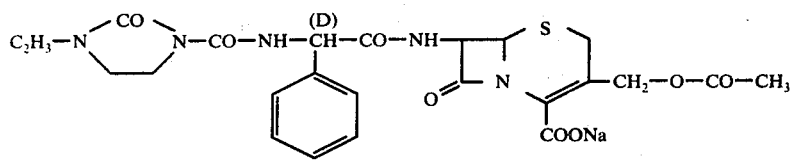

This sodium salt of a cephalosporin was prepared in the manner described in Example 3 from 2.2 parts by wt. of cephaloglycine and 0.8 part by wt. of 1-chlorocarbonyl-2-oxo-3-ethyl-imidazolidine.

Yield: 1.9 parts by wt. of sodium 7-{D-α-[(3-ethyl-2-oxo-imidazolidin-1-yl)-carbonylamino]-phenylacetamido}-3-acetoxymethyl-ceph-3-em-4-carboxylate.

β-Lactam content: about 82%.

IR bands in the carbonyl region 1,780, 1,720, 1,675, 1,610 and 1,540 cm$^{-1}$.

The sodium salt of the cephalosporin contained about 2 mols of water and was contaminated by about 0.5 mol of sodium 2-ethylhexanoate. This was taken into account in the calculated analytical data.

Calculated: C 49.0, H 5.5, N 10.2, S 4.7, Found: C 48.7, H 5.5, N 10.4, S 4.9.

1-Chlorocarbonyl-2-oxo-3-ethyl-imidazolidine, melting point (of the not quite analytically pure substance) 54° C, which was used as the starting material, was obtained from 1-ethyl-2-oxo-imidazolidine by reaction with phosgene in tetrahydrofurane. 1-Ethyl-2-oxo-imidazolidine was obtained from 2-oxo-imidazolidine by reaction with ethyl iodide in tert.-butanol/Na tert.-butanolate. It has a boiling point of b.p. = 70°–96° C at 0.7–1.0 mm.

EXAMPLE 5

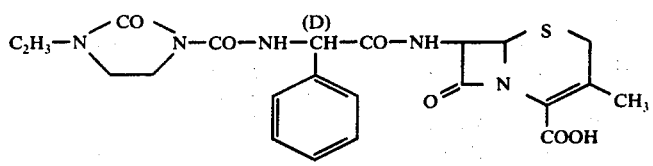

This sodium salt of a cephalosporin was prepared in the manner described in Example 3 from 2.1 parts by wt. of cephalexin and 1.0 part by wt. of 1-chlorocarbonyl-2-oxo-3-ethyl-imidazolidine and was isolated as the free acid. The cephalosporin acid separated out, on acidification, as a slimy precipitate which was insoluble in the ether/ethyl acetate phase.

Yield: 3.1 parts by wt. of 7-{D-α-[(3-ethyl-2-oxo-imidazolidin-1-yl)-carbonylamino]-phenylacetamido}-3-methyl-ceph-3-em-4-carboxylic acid.

β-Lactam content: about 81%.

NMR signals at τ = 2.4–2.8 (5H); 4.1–4.4 (2H); 4.9–5.1 (1H); 6.1–6.9 (8H); 7.8–8.0 (3H) and 8.7–9.0 ppm (3H).

IR bands in the carbonyl region: 1,770, 1,710, 1,650 and 1,530 cm$^{-1}$.

EXAMPLE 6

A)

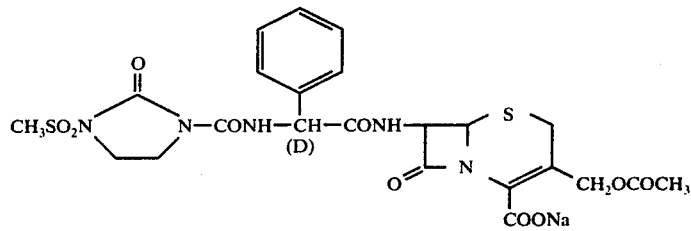

Sodium 7-{D-α-[(2-oxo-3-mesyl-imidazolidin-1-yl)-carbonylamino]-phenylacetamido}-3-acetoxymethyl-ceph-3-em-4-carboxylate was prepared, in 71% yield, in the manner described in Example 1 from 1.3 parts by wt. of cephaloglycine dihydrate and 0.77 part by wt. of 1-chlorocarbonyl-2-oxo-3-mesyl-imidazolidine.

IR bands at 3,230, 1,760, 1,727, 1,654, 1,598, 1,518 1,250, 1,230, 1,157, 1,120 and 973 cm$^{-1}$.

NMR signals at τ = 2.3–2.7 (m, 5H); 4.25 + 4.95 (AX, 1H + 1H); 4.4 (s, 1H); 5.1 (d, 2H); 6.05 (s, 4H); 6.6 (m, 5H) and 7.9 ppm (3H).

The electropherogram only shows one spot with antibiotic activity. B. 1-Chlorocarbonyl-3-methylsulphonyl-imidazolidinone-(2):

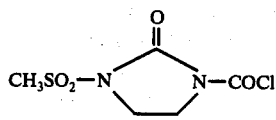

16.4 parts by wt. of 1-methylsulphonyl-imidazolidinone-(2) in dioxane were boiled with 27 parts by wt. of trimethylchlorosilane and 20 parts by wt. of triethylamine for 3 days. The triethylamine hydrochloride which precipitated was filtered off, 11 parts by wt. of phosgene were added to the filtrate and the mixture was left to stand overnight at room temperature. It was then evaporated to dryness and the residue was recrystallized from boiling acetone.

Yield: 70%; m.p. = 178°.

Calculated: C 26.5, H 3.1, Cl 15.7, N 12.4, S 14.1, Found: C 27.2, H 3.4, Cl 15.3, N 12.0, S 14.1.

NMF signals at $\tau$ = 5.6–6.2 (4H) and 6.6 ppm (3H).

IR bands at 3,010, 1,807, 1,721, 1,360, 1,165, 984 and 742 $cm^{-1}$.

The same product can also readily be prepared from 1-methylsulphonylimidazolidinone-(2) and excess phosgene in methylene chloride. C. N-Methylsulphonyl-imidazolidinone-2:

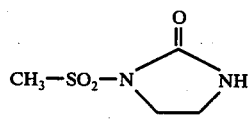

Instruction 1

63 parts by wt. of methanesulphochloride were added dropwise at room temperature to a suspension of 43 parts by wt. of imidazolidinone-2 in 400 parts by vol. of dry tetrahydrofurane and the mixture was stirred for 1 hour at 30°–40° C and then heated for 1 hour under reflux. The solvent was then distilled off i.v. and the residue was kept for 1 hr. at 60° C under an oil pump. The residue was then recrystallized from warm acetone.

Yield: 25%; m.p. 193° C.

Calculated: C 29.3, H 4.9, N 17.1, S 19.5, Found: C 29.0, H 5.0, N 17.2, S 19.6.

IR bands at 3,250, 3,115, 1,715, 1,350 and 1,160 $cm^{-1}$.

NMR signals at $\tau$ = 2.4 (1H); 6.2(2H); 6.5 (2H) and 6.8 ppm (3H).

Instruction 2

80 parts by wt. of methanesulphochloride were added dropwise over the course of 30 mins., while stirring, to a suspension of 43 parts by wt. of imidazolidinone-2 in 300 parts by vol. of dry tetrahydrofurane, and 56 parts by wt. of triethylamine were then added in such a way that the internal temperature was about 35°–40° C. The mixture was stirred for a further 2 hrs. at 45° C, the solvent was then stripped off in vacuo, the residue which remained was extracted with twice 150 parts by vol. of chloroform, and the crystals which remained were recrystallized from methanol.

Yield: 49%.

The product agrees, in respect of m.p. and IR spectrum, with the N-methylsulphonylimidazolidinone-2 described above.

EXAMPLE 7

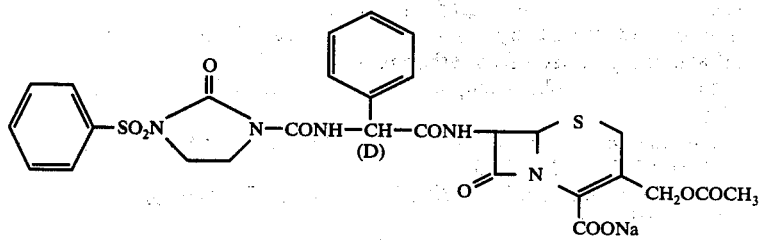

Sodium 7-{D-α-[(2-oxo-3-phenylsulphonyl-imidazolidin-1-yl)-carbonylamino]-phenylacetamido}-3-acetoxymethyl-ceph-3-em-4-carboxylate was prepared in 64% yield from 1.3 parts by wt. of cephaloglycine dihydrate and 1.0 part by wt. of 1-chlorocarbonyl-2-oxo-3-phenylsulphonyl-imidazolidine, in the manner described in Example 1.

IR bands at 3,250, 1,760, 1,728, 1,670, 1,604, 1,515, 1,240, 1,170 and 1,118 $cm^{-1}$.

NMR signals at $\tau$ = 0.5 (d, 1H); 1.25 (d, 1H); 1.7–2.0 (m, 2H); 2.0–2.3 (m, 3H); 2.3–2.8 (m, 5H); 4.1–4.5 (m, 2H); 4.8–5.1 (m, 3H); 6.05 (broad s, 4H); 6.6 (m, 2H) and 7.9 ppm (s, 3H) in DMSO-$d_6$).

β-Lactam content, according to NMR spectrum and IR spectrum, 80%–90%.

B)

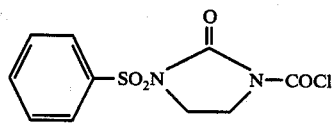

A mixture of 80 parts by wt. of 1-phenylsulphonyl-2-oxo-imidazolidine, 69 parts by wt. of phosgene, 31.6 parts by wt. of pyridine and 350 parts by vol. of methylene chloride, which had been prepared at 0° C, was stirred overnight at room temperature and then evaporated to dryness. The residue was then suspended in 500 parts by vol. of ice water and filtered off. This residue was taken up in 500 parts by vol. of methylene chloride and the solution was dried over MgSO$_4$, filtered and again evaporated to dryness. The residue was recrystallized from acetone/petroleum ether. M.p. = 161° C. Yield, 64% of 1-chlorocarbonyl-2-oxo-3-phenylsulphonyl-imidazolidine.

Calculated: C 41.6, H 3.5, Cl 12.3, N 9.7, S 11.1, Found: C 41.6, H 3.0, Cl 12.2, N 9.7, S 10.7.

IR bands at 1,802, 1,732, 1,318 and 1,200 $cm^{-1}$ (in Nujol).

NMR signals at $\tau$ = 1.8–2.1 (2H); 2.1–2.5 (3H) and 5.7–6.1 ppm (4H).

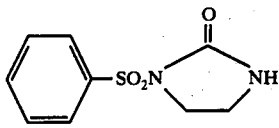 C)

A mixture of 86 parts by wt. of 2-oxo-imidazolidine, 194 parts by wt. of benzenesulphonyl chloride, 800 parts by vol. of tetrahydrofurane, 500 parts by vol. of chloroform and 101 parts by wt. of triethylamine was stirred overnight at 50° C and then evaporated to dryness in vacuo. The residue was gradually poured, while stirring, into 1,000 parts by vol. of ice water, then filtered off and recrystallized from ethanol. M.p. = 155° C.

Yield of 1-phenylsulphonyl-2-oxo-imidazolidine: 35%.

Calculated: C 47.7, H 4.4, N 12.4, S 14.2, Found: C 47.8, H 4.5, N 12.2, S 14.3.

IR bands at 3,280, 1,740, 1,700, 1,280, 1,178, 1,095 and 1,060 cm$^{-1}$ (in Nujol).

NMR signals at $\tau$ = 1.8–2.6 (6H); 6.1 (2H) and 6.7 ppm (2H) (in DMSO-$d_6$).

EXAMPLE 8

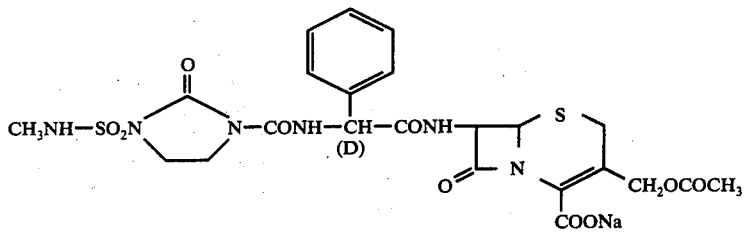

This cephalosporin was prepared in the manner described in Example 1 from 1.5 parts by wt. of cephaloglycine dihydrate and 0.95 part by wt. of 1-chlorocarbonyl-2-oxo-3-methylaminosulphonyl-imidazolidine.

Yield of sodium 7-{D-α-[(2-oxo-3-methylaminosulphonyl-imidazolidin-1-yl)-carbonylamino]-phenylacetamido}-3-acetoxy-methyl-ceph-3-em-4-carboxylate: 52%.

IR bands at 3,220, 1,760, 1,718, 1,665, 1,600, 1,518 1,252, 1,230 and 1,175 cm$^{-1}$.

NMR signals at $\tau$.=2.4–2.9 (m, 5H); 4.35 + 5.05 (AX, 1H + 1H); 4.45 (s, 1H); 5.1 (d,2H); 6.15 (s, 4H); 6.6 (AB, 2H) and 8.0 ppm (3H).

β-Lactam content according to IR spectrum and NMR spectrum: 85–90%.

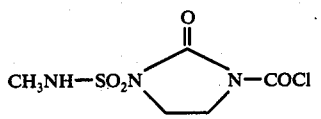 B)

A solution of 7.1 parts by vol. of phosgene in 30 parts by vol. of tetrahydrofurane was added dropwise to a suspension of 17.9 parts by wt. of 1-methylaminosulphonyl-2-oxo-imidazolidine in 100 parts by vol. of methylene chloride at 10° C. 7.9 parts by vol. of pyridine in 30 parts by vol. of tetrahydrofurane were then added dropwise at 10° C, the mixture was stirred for 30 minutes at 10° C and 3 hrs. at room temperature and evaporated to dryness in vacuo, the residue was taken up in 100 parts by vol. of methylene chloride and the methylene chloride solution was shaken with 25 parts by vol. of water and dried over MgSO$_4$. After evaporating the solution in vacuo, the residue was recrystallized from benzene. M.p. = 79°–80° C.

Yield: 80% of 1-chlorocarbonyl-2-oxo-3-methylaminosulphonyl imidazolidine.

IR bands at 3,250, 1,795, 1,720, 1,285, 1,232, 1,175, 1,140 and 955 cm$^{-1}$ (in Nujol).

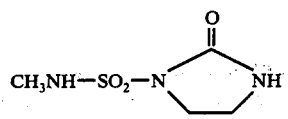 C)

13.0 parts by wt. of N-chlorosulphonyl-methylamine in 20 parts by vol. of acetonitrile were added dropwise to 8.6 parts by wt. of 2-oxo-imidazolidine in 70 parts by vol. of acetonitrile at 15° C, 10.0 parts by wt. of triethylamine were then added dropwise and the mixture was stirred for 1 hr. at room temperature and 1 hr. at 50° C. After cooling to room temperature, the mixture was filtered, the residue was washed with acetonitrile and the combined acetonitrile phases were evaporated to dryness in vacuo; the residue was recrystallized from acetone.

Yield: 50%, m.p. = 182° C.

Renewed recrystallization from isopropanol gave 1-methylaminosulphonyl-2-oxo-imidazolidine of m.p. = 184° C in 44% yield.

Calculated: C 26.8, H 5.0, N 23.2, S 17.9, Found: C 27.0, H 5.1, N 23.3 , S 17.6

IR bands at 3,240 1,704, 1,260, 1,170, 1,130 and 1,080 cm$^{-1}$ (in Nujol).

EXAMPLE 9

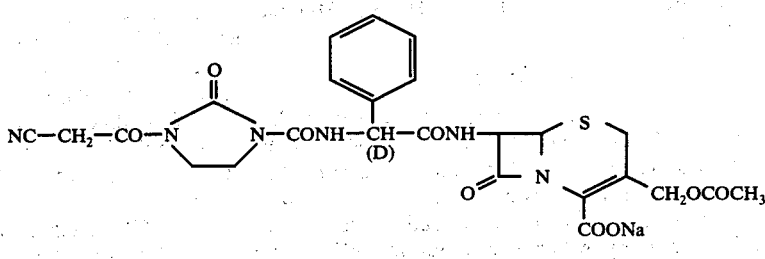 A)

2.2 parts by wt. of cephaloglycine dihydrate were suspended in 30 parts by vol. of methylene chloride, 1.3. parts by wt. of triethylamine were added, the mixture was cooled to −20° and a solution of 1.0 part by wt. of 1-chlorocarbonyl-3-cyanmethylcarbonyl-imidazolidinone-(2) in 6 parts by vol. of methylene chloride was added. After stirring for 30 mins. at −10° C and 30 mins. at 20° C, the methylene chloride was stripped off. Working up to give sodium 7-{D-α-[(2-oxo-3-cyanoacetyl-imidazolidin-1-yl)-carbonylamino]-phenylacetamido}-3-acetoxy-methyl-ceph-3-em-4-carboxylate was carried out as in Example 3.

β-Lactam content: 70-75%.

Characteristic IR bands: 2,210, 1,760, 1,670 and 1,610 cm$^{-1}$.

B) 1-Chlorocarbonyl-3-cyanomethylcarbonyl-imidazolidinone-(2):

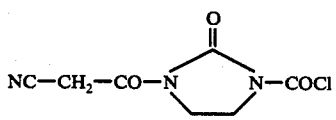

10.0 parts by wt. of 1-cyanomethylcarbonyl-imidazolidinone -(2) were suspended in 100 parts by vol. of methylene chloride, the suspension was cooled to −10° C, 9.2 parts by wt. of phosgene were added and the mixture was stirred for 30 mins. at 0° C. 7.7 parts by wt. of pyridine were added dropwise and the mixture was stirred overnight. The pyridine hydrochloride which precipitated was filtered off, the filtrate was concentrated and the residue was recrystallized from acetone. C) 1-Cyanomethylcarbonylimidazolidinone-(2):

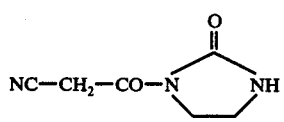

8.6 parts by wt. of imidazolidinone-(2) were suspended in 30 parts by vol. of tetrahydrofurane and a solution of 10.4 parts by wt. of cyanoacetyl chloride in 20 parts by wt. of tetrahydrofurane was added dropwise with cooling, the temperature being kept at between 25° and 30° C. Thereafter the hydrogen chloride formed was expelled by means of a stream of nitrogen (approx. 1 hr.) and the reaction product was filtered off. After recrystallization from acetonitrile, 6.3 parts by wt. (52%) of 1-cyanomethylcarbonyl-imidazolidinone-(2) of m.p. 214°-217° were obtained.

Calculated: C 47.06; H 4.61; N 27.44 Found: C 47.2; H 4.8; N 27.5.

Characteristic IR bands: 2,260, 1,750 and 1,670 cm$^{-1}$.

NMR signals in δ (DMSO): 7.80 (s, 1H); 4.35 (s, 2H); m centered at 3.84 (2H) and m centered at 3.35 (2H).

EXAMPLE 10

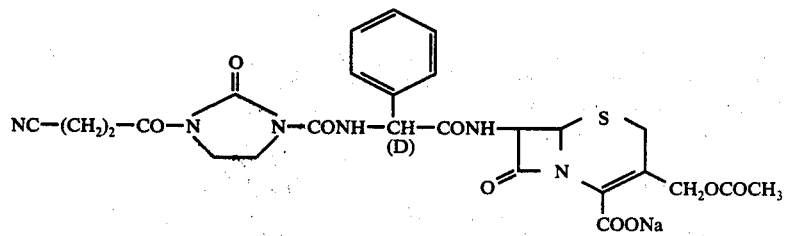

A)

2.2 parts by wt. of cephaloglycine dihydrate were reacted with 1.1 parts by wt. of 1-chlorocarbonyl-3-β-cyano-propionyl-imidazolidinone-(2) in the manner indicated in Example 9A. 3.2 parts by wt. of reaction product (71%) of dec.p. 203° C of 90% β-lactam content: sodium 7-{D-α-[(2-oxo-3-β-cyanopropionyl-imidazolidin-1-yl)-carbonylamino]-phenyl-acetamido}acetamido}-3-acetoxymethyl-ceph-3-em-4-carboxylate were obtained.

Calculated: C 50.32, H 4.06, N 13.54, S 5.17, Found: C 49.6, H 4.2, N 13.6, S 5.2.

Characteristic IR bands: 2,250, 1,765, 1,735, 1,675 and 1,610 cm$^{-1}$. B) 1-Chlorocarbonyl-3-β-cyanopropionyl-imidazolidinone-(2):

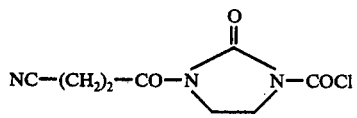

8.5 parts by wt. of 1β-cyanopropionyl-imidazolidinone- (2) were reacted with 9.9 parts by wt. of phosgene as in Example 9B. The product was triturated with a little cold water, filtered off and dried. 5.1 parts by wt. (44%) of dec.p. 127°-130° C.

Calculated: C 41.85, H 3.51, N 18.30, Cl 15.44, Found: C 42.2, H 3.4, N 17.9, Cl 15.8.

Characteristic IR bands: 2,520, 1,795, 1,715 and 1,685 cm$^{-1}$. C) 1-β-cyanopropionyl-imidazolidinone-(2):

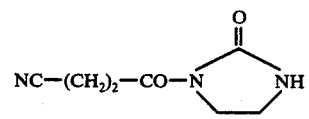

5.3 parts by wt. of ⊖-cyanopropionic acid chloride were reacted with 3.9 parts by wt. of imidazolidinone-(2) as in Example 9C. Recrystallization from acetone; 3.6 parts by wt. (48%) of m.p. 130°-132° C.

Calculated: C 50.30, H 5.43, N 25.15, Found: C 50.2, H 5.5. M 25.1.

Characteristic IR bands: 2,250, 1,750, and 1,670 cm$^{-1}$.

NMR signals in δ(DMSO): 7.62 (s, 1H); 3.80 (t, 2H); m centered at 3.3 (4H) and 2.67 (t, 2H).

EXAMPLE 11

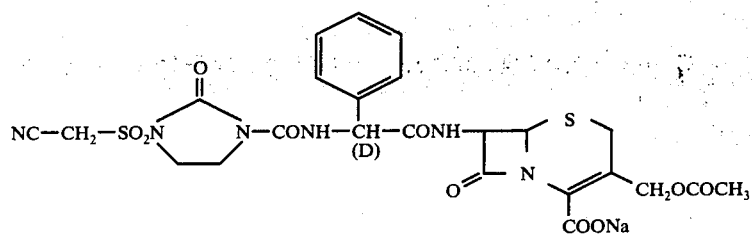

2.2 parts by wt. of cephaloglycine dihydrate were reacted with 1.3 parts by wt. of 1-chlorocarbonyl-3-cyano-methylsulphonyl-imidazolidinone-(2), in the manner indicated in Example 9A, to give sodium 7-{D-α-[(2-oxo-3-cyanomethyl-sulphonyl-imidazolidin-1-yl)-carbonylamino]-phenylacetamido}-3-acetoxymethyl-ceph-3-em-carboxylate (β-lactam content, according to the IR spectrum, 70%–75%).

Characteristic IR bands: 2,210, 1,760, 1,735, 1,675 and 1,610 cm$^{-1}$.

B)

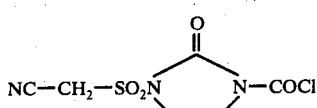

1-Chlorocarbonyl-3-cyanomethylsulphonyl-imidazolidinone-(2).

9.5 parts by wt. of 1-cyanomethylsulphonyl-imidazolidinone -(2) were reacted with 9.9 parts by wt. of phosgene as in Example 9B.

C)

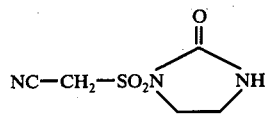

1-Cyanomethylsulphonyl-imidazolidinone-(2).

13.4 parts by wt. of cyanomethylsulphonyl chloride were reacted with 8.6 parts by wt. of imidazolidinone-(2) as in Example 9C. Recrystallization from methyl ethyl ketone; 4.1 parts by wt. (21.6%) of dec.p. 168°–172° C.

Calculated: C 31.75, H 3.73, N 22.21, S 16.95, Found: C 31.8, H 3.8, N 22.2, S 16.9

Characteristic IR bands: 2,260, and 1,730 cm$^{-1}$.

NMR signals in δ(acetone): 4.90 (s, 2H); 4.12 (t, 2H) and 3.64 (t, 2H).

EXAMPLE 12

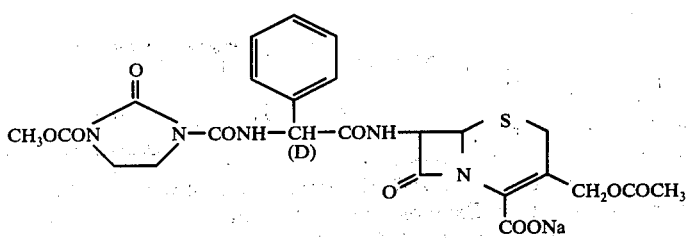

Sodium 7-{D-α-[(2-oxo-3-methoxycarbonyl-imidazolidin-1-yl)-carbonylamino]-phenylacetamido}-3-acetoxymethyl-ceph-3-em-4-carboxylate was prepared in 23% yield, in the manner described in Example 1, from 1.55 parts by wt. of 1-chloro-carbonyl-2-oxo-3-methoxycarbonyl-imidazolidine and 3.0 parts by wt. of cephaloglycine.

IR bands at 3,270, 1,760, 1,750, 1,670, 1,610 and 1,525 cm$^{-1}$ (in Nujol).

NMR signals at τ = 2.3–2.9 (5H), 4,25 (1H), 4.43 (1H), 4.95 (1H), 5.3 (2H), 5.9–6.4 (7H), 6.6 (2H) and 7.8 ppm (3H) in D$_2$O). B) 1-Chlorocarbonyl-2-oxo-3-methoxycarbonyl-imidazolidine

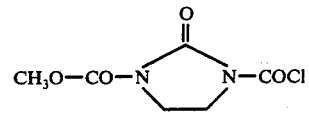

This carbamic acid chloride was prepared in the manner described in Example 14B from 8 parts by wt. of N-methoxy-carbonyl-imidazolidone-2, 9.7 parts by wt. of trimethylchlorosilane, 9 parts by wt. of triethylamine and 6.2 parts by wt. of phosgene.

Yield: 72%. M.p. = 129° C. Calculated C 34.8, H 3.4, Cl 17.1, N 13.6, C 34.8, H 3.4, Cl 17.1, N 13.6.

IR bands at 1,820, 1,737, 1,690 and 1,260 cm$^{-}$.

NMR signals at τ= 5.7–6.3 (4H) amd 6.1 ppm (3H).

C) N-Methoxycarbonyl-imidaxolidone-2

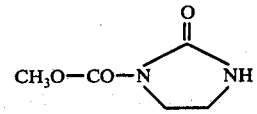

14.9 parts by wt. of N-chlorocarbonyl-imidazolidone-2 were introduced into 70 parts by vol. of ice-cold methanol and the mixture was stirred for 1 hr. at room temperature and then for 1 hr. at 40°-50° C. After stripping off the excess methanol, the residue was recrystallized from acetone.

Yield: 55%. M.p. = 185° C.

Calculated: C 41.6, H. 5.5, N 19.4. Found: C 41.8, H 4.8, N 19.2.

IR bands at 3,320, 1,745 and 1,670 cm$^{-1}$.

EXAMPLE 13

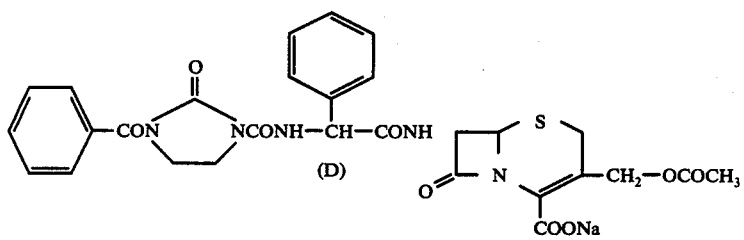

Sodium 7-{D-α-[(2-oxo-3-benzoyl-imidazolidin-1-yl)-carbonylamino]-phenylacetamido}-3-acetoxymethyl-ceph-3-em-4-carboxylate was prepared in the manner described in Example 1 from 1.9 parts by wt. of 1-chlorocarbonyl-2-oxo-3-benzoyl-imidazolidine and 3.0 parts by wt. of cephaloglycine.

Yield: 67.5%

IR bands at 3,300, 1,750, 1,730, 1,665, 1,615 and 1,505 cm$^{-1}$ (in Nujol).

NMR signals at τ=2.2–2.9 (10H), 4.25 (1H), 4.4 (1H), 5.0 (1H), 5.3 (2H), 5.8–6.3 (4H), 6.5 (1H), 6.9 (1H) and 7.98 ppm (3H) (in D$_2$).

water was extracted once more with chloroform and the combined organic phases were washed with water, dried over MgSO$_4$ and evaporated. The residue was recrystallized from ethyl acetate/ether.

Yield: 30%. M.p. = 169.70° C.

Calculated: C 63.2, H 5.3, N 14.8, Found: C 63.0, H 5.3, N 14.8.

IR bands at 3,190, 3,110, 1,742, 1,718 and 1,655 cm$^{-1}$.

NMR signals at τ =2.2.-2.9 (5H), 3.9 (1H), 6.0 (2H) and 6.6 ppm (2H).

EXAMPLE 14

A)

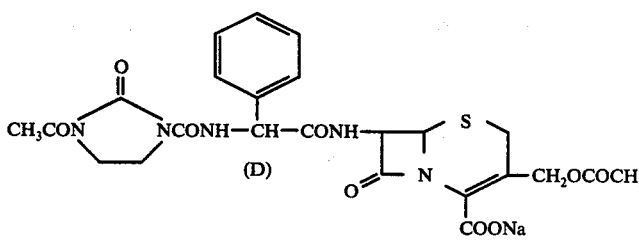

B. 1-Chlorocarbonyl-2-oxo-3-benzoyl-imidazolidine

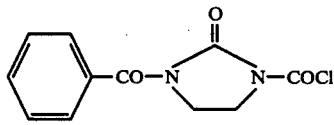

This carbamic acid chloride was prepared in the manner described in Example 14B from 4.8 parts by wt. of N-benzoylimidazolidone-2, 4.4 parts by wt. of trimethylchlorosilane and 2.8 parts by wt. of phosgene.

Yield: 100%. M.p. = 153°–154° C.

Calculated: C 52.2, H 3.6, Cl 14.0, N 11.1, Found: C 51.2, H 4.4, Cl 13.2, N 11.1.

IR bands at 3,060, 1,768, 1,725 and 1,672 cm$^{-1}$.

NMR signals at τ = 2.5 (5H) and 6.0 ppm (4H).

C. N-Benzoyl-imidazolidone-2

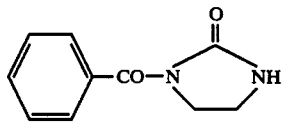

15.5 parts by wt. of benzoyl chloride in 30 parts by vol. of tetrahydrodurane uere added overthe course of 15 mins. to 8.6 parts by wt. of imidazolidone-2 in 100 parts by vol. of dry tetrahydrofurane at 5°–10° C and the mixture was then stirred for 3 hrs. at 10° C. The solvent was stripped off, the residue was shaken with a mixture of chloroform and aqueous NaHCO$_3$ solution for 15 mins., the chloroform was separated off, the Sodium 7-{D-α-[(2-oxo-3-acetyl-imidazolidine-1-yl)-carbonylamino]-phenylacetamido}-3-acetoxymethyl-ceph-3-em-4-carboxylate was prepared in the manner described in Example 1 from 1.43 parts by wt. of 1-chlorocarbonyl-2-oxo-3-acetylimidazolidine and 3.0 parts by wt. of cephaloglycine.

Yield 65%.

IR bands at 3,260, 1,750, 1,735, 1,680, 1,615, 1,520 1,315, 1,260, 1,240-31 1,215 and 750 cm$^{-1}$ (in Nujol).

NMR signals at τ =0.35 (1H), 0.9 (1H), 2.3–2.8 (5H), 4.1-4.55 (2H), 5.03 (3H), 6.2 (5H), 6.65 (2H), 7.5 (3H) and 7.9 ppm (3H) (in dimethylformamide-d$_7$).

Calculated: C 49.5, H 4.1, N 12.0, S 5.5, Found C 48.7, H 5.3, N 11.4, S 5.6.

B. 1-Chlorocarbonyl-2-oxo-3-acetyl-imidazolidine

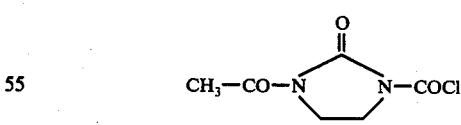

20 parts by wt. of N-acetyl-imidazolidone-2 were mixed with 24 parts by wt. of triethylamine and 150 parts by vol. of dry benzene and 27 parts by wt. of trimethylchlorosilane in 40 parts by vol. of benzene were added dropwise over the course of 30 mins. While stirring at room temperature. The mixture was then boiled for 18 hrs. under reflux with exclusion of moisture and after cooling the triethylamine hydrochloride which had precipitated was filtered off (22 parts by wt. = 100%) and carefully washed with dry benzene. The benzene solution thus obtained was mixed with a solution of 17 parts by wt. of phosgene in 50 parts by vol. of benzene at 5° C and the mixture was left to stand overnight at 5° C. The solvent was then stripped off in vacuo and the residue was dried under an oil pump. It was recrystallized from an acetone/pentane mixture.

Yield: 81%. M.p. = 104° C
Calculated: C 37.7, H 3.7, Cl 18.6, N 14.7, C 39.3, H 4.3, Cl 17.7, N 14.7.
IR bands at 1,798, 1,740, 1690 and 1,660 cm⁻¹.
NMR signals at $\tau$ = 5.65-6.3 (4H) and 7.45 ppm (3H).
According to the NMR spectrum, the product still contained 5-10% of N acetyl-imidazolidone, but this does not interfere with the reaction with cephaloglycine.

C. N-Acetyl-imidazolidone-2

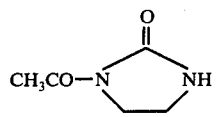

23.6 parts by wt. of acetyl chloride in 100 parts by vol. of tetrahydrofurane were added dropwise over the course of 60 mins. to a suspension of 25.8 parts by wt. of imidazolidone-2 in 350 parts by vol. of dry tetrahydrofurane at 0° C.

The mixture was stirred for 3 hrs. at room temperature, dry air was then blown through the solution for a period and the residue was then recrystallized from boiling nitromethane.

Yield: 52%. M.p. = 188° C.
Calculated: C 46.9, H 6.9, N 21.9 Found: C 47.0, H 6.2, N 22.5.
IR bands at 3,230, 1,730 and 1,640 cm⁻¹.
NMR signals at $\tau$ = 6.2 (2H), 6.5 (2H) and 7.6 ppm (3H).

EXAMPLE 15

IR bands at 3,310, 3,250, 1,775, 1,750, 1,730, 1,660, 1,520, 1,325, 1,260-1,220 and 753-738 cm⁻¹ (in Nujol).
NMR signals at $\tau$ = 0.55 (1H), 1.0 (1H), 1.93 (1H), 2.4-2.75 (6H), 3.2 (1H), 4.1-4.6 (2H), 5.05 (3H), 6.1 (4H), 6.7 (2H) and 7.98 ppm (3H) in dimethylformamide-d₇).

B. 1-Chlorocarbonyl-2-oxo-3-furoyl-(2)-imidazolidine

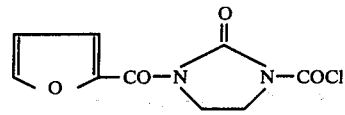

This carbamic acid chloride was prepared in the manner described in Example 14B from 9 parts by wt. of N-furoyl(2)imidazolidone-2, 8.7 parts by wt. of trimethylchlorosilane and 6.0 parts by wt. of phosgene.

Recrystallization from benzene.
Yield: 55%. M.p. = 119° C
Calculated: C 44.5, H 2.9, Cl 14.6, N 11.5, Found: C 45.0, H 3.6, Cl 13.4, N 11.5.
IR bands at 3,150, 3,100, 1,800, 1,745, 1,715, 1,650, 1,620 and 1,255 cm⁻¹.
NMR signals at $\tau$ = 2.3 (1H), 2.5 (1H), 3.4 (1H) and 5.9 ppm (4H).

C. N-Furoyl-(2)-imidazolidone-2

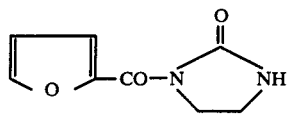

This substance was prepared in the manner described in Example 13C from imidazolidone-2 and furane-α-carboxylic acid chloride. Instead of being stirred at 10° C, the mixture was stirred for a further 3 hrs. at 30°-40° C. Recrystallization from nitromethane.

Yield: 53%. M.p. = 144-6° C.

A)

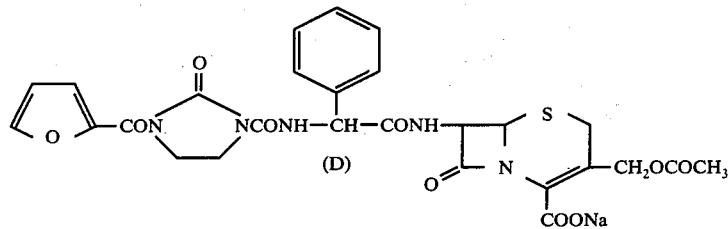

Sodium 7-{D-α-[(2-oxo-3-furoyl-(2)-imidazolidin-1-yl)-carbonylamino]-phenylacetamido}-3-acetoxymethyl-ceph-3-em-4-carboxylate was prepared in the manner described in Example 1 from 1.82 parts by wt. of 1-chlorocarbonyl-2-oxo-3-furoyl-(2)-imidazolidine and 3.0 parts by wt. of cephaloglycine.

Yield: 78.6%

Calculated: C 53.2, H 4.5, N 15.6, Found: C 51.2, H 4.5, N 15.3.
IR bands at 3,245, 3,120, 1,740, 1,622, 1,500, 1,257 and 1,240 cm⁻¹.
NMR signals at $\tau$ = 2.25 (1H), 2.6 (1H), 3.35 (1H), 6.0 (2H) and 6.4 ppm (2H).

EXAMPLE 16

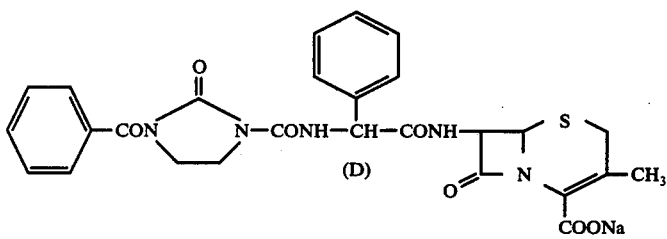

Sodium 7-{D-α-[(2-oxo-3-benzoyl-imidazolidin-1-yl)-carbonylamino]-phenylacetamido}-3-methyl-ceph-3-em-4-carboxylate was prepared in the manner described in Example 1 from 2.3 parts by wt. of 1-chlorocarbonyl-2-oxo-3-benzoyl-imidazolidine and 3.0 parts by wt. of cephalexin.

Yield 79%.

IR bands at 3,300, 1,740, 1,660, 1,600, 1,500, 1,320, 1,250 and 1,230 cm$^{-1}$ (in Nujol).

NMR signals at τ = 0.6 (1H), 1.0 (1H), 2.1-2.8 (10H), 4.05-4.6 (2H), 5.07 (1H), 6.0 (4H), 6.85 (2H) and 7.95 ppm (3H).

EXAMPLE 17

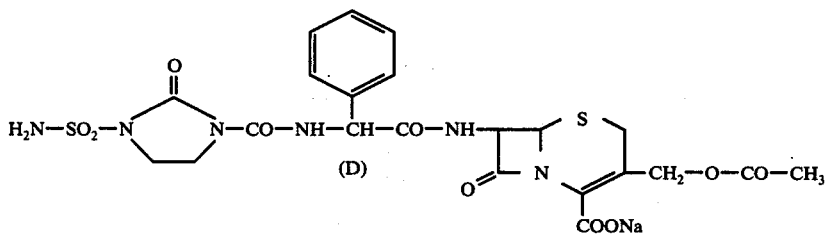

Sodium 7-{D-α-[(2-oxo-3-sulphamyl-imidazolidin-1-yl)-carbonylamino]-phenylacetamido}-3-acetoxymethyl-ceph-3-em-4-carboxylate was prepared in a yield of 0.5 part by wt. from 2.2 parts by wt. of cephaloglycine dihydrate and 2.2 parts by wt. of 1-chlorocarbonyl-2-oxo-3-sulphamyl-imidazolidine (added as a solution in 5 parts by vol. of acetonitrile), in the manner described in Example 3. At the same time, the free acid of the same cephalosporin was obtained in a yield of 2.4 parts by wt. If this free acid is dissolved in 7 parts by vol. of dimethylformamide and this solution is added dropwise to a mixture of 4.8 parts by vol. of 1-molar sodium 2-ethylhexanoate solution in ether (containing methanol), 120 parts by vol. of ether and 12 parts by vol. of ethanol, a further 1.8 parts by wt. of the sodium salt of the cehalosporin are obtained.

IR bands (in the carbonyl region) at 1,755, 1,720, 1,655, 1,600 and 1,520 cm$^{-1}$ (in Nujol).

NMR signals at τ = 2.3–2.75 (5H), 4.1–4.45 (2H), 4.9-5.2 (3H), 5.9–6.2 (4H), 6.5-6.65 (2H) and 7.9 ppm (3H) (CD$_3$OD).

It can be deduced from the NMR spectrum that the substance contains about 3.7 mols of H$_2$O and 0.7 mol of dimethylformamide. This was taken into account in the calculated analytical data below:

Calculated: C 39.5, H 4.2, N 12.8, S 8.7, Found: C 40.0, H 4.2, N 12.3, S 8.2.

B. 1-Chlorocarbonyl-2-oxo-3-sulphamyl-imidazolidine

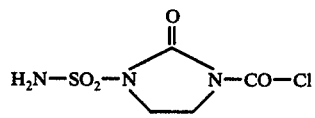

A solution of 17.8 parts by vol. of triethylamine in 30 parts by vol. of dichloromethane was added dropwise over the course of 2 hrs. to a mixture of 100 parts by vol. of dichloromethane, 6.15 parts by vol. of (condensed) phosgene and 7.0 parts by wt. of 1-sulphamyl-2-oxo-imidazolidine at 20° C and the mixture was then left to stand for 17 hrs. The precipitate present was removed by filtration, the filtrate was concentrated by evaporation in vacuo and the residue was repeatedly extracted with ethyl acetate at 20° C. The ethyl acetate extracts were combined. On evaporation, they left a hard varnish. The IR spectrum showed a strong acid chloride band at 1,805 cm$^{-1}$ (Nujol). Furthermore, it could be seen from the IR spectrum that the substance still contained considerable amounts of the starting product.

C. 1-Sulphamyl-2-oxo-imidazolidine

A solution of 36.3 parts by wt. of amidosulphochloride in 90 parts by vol. of acetonitrile was added to a suspension of 25.8 parts by wt. of 2-oxo-imidazolidine in 180 parts by vol. of acetonitrile at 10° C. The mixture was then stirred for 15 mins. without further cooling and subsequently warmed to 50° C for 1 hr. After cooling, the precipitate present was filtered off, stirred for some minutes in 500 parts by vol. of water and filtered off, the filtrate was completely concentrated by evaporation in vacuo and the residue was extracted by boiling with 400 parts by vol. of isopropanol, then filtered off, suspended in 30 parts by vol. of water, again filtered off, twice washed with 10 parts by vol. of water at a time, and dried.

Yield: 15 parts by wt. Dec.p. 188° C
Calculated: C 21.8, H 4.2, N 25.5, S 19.4, Found: C 21.8, H 4.3, N 25.4, S 19.6.

EXAMPLE 18

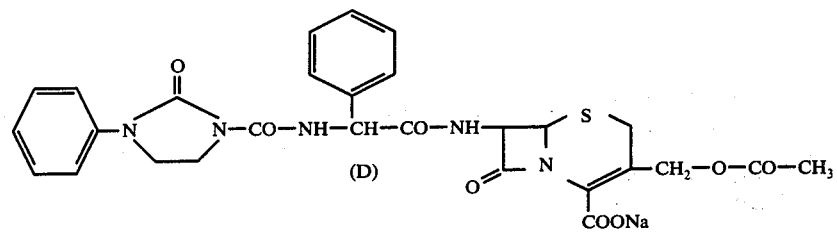

Sodium 7-{D-α-[(2-oxo-3-phenyl-imidazolidin-1-yl)-carbonylamino]-phenylacetamido}-3-acetoxymethyl-ceph-3-em-4-carboxylate was prepared in the manner described in Example 3 from 2.2 parts by wt. of cephaloglycine dihydrate and 1.0 part by wt. of 1-chlorocarbonyl-2-oxo-3-phenyl-imidazolidine and on acidification to pH 2 was first obtained in the form of a sparingly soluble precipitate of the free acid (3.5 parts by wt.). This was dissolved in 3.5 parts by vol. of dimethylacetamide, the solution was clarified by removing insoluble matter through filtration through a little Al₂O₃, the calculated amount of 1-molar sodium 2-ethylhexanoate solution in ether containing methanol was added to the filtrate and this mixture was stirred into 100 parts by vol. of ether. The sodium salt which precipitated was filtered off, washed with a mixture of 50 parts by vol. of ether and 10 parts by vol. of methanol and dried.

Yield: 1.6 parts by wt.

The substance crystallizes with 1.5 mols of H₂O. This was taken into account in the calculated analytical data:

Calculated: C52.4, H 4.5, N 10.9, S 5.0 Found: C 52.4, H 5.5, N 10.9, S 5.0

IR bands (in the carbonyl region): 1,760, 1,715, 1,655, 1,600 and 1,525 cm⁻¹ (in Nujol).

NMR signals at τ = 2.1–2.9 (10H), 4.1–4.5 (2H), 4.9–5.15 (3H), 5.9–6.1 (4H), 6.5–6.7 (2H) and 7.95 ppm (3H) (in dimethylformamide-d₇/CD₃OD).

B. 1-Chlorocarbonyl-2-oxo-3-phenyl-imidazolidine

A)

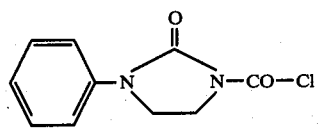

16.2 parts by wt. of 1-phenyl-2-oxo-imidazolidine were suspended in 160 parts by vol. of tetrahydrofurane and 12.0 parts by wt. of phosgene, dissolved in 30 parts by vol. of tetrahydrofurane, were added dropwise at 10° C. The mixture was then stirred for a further 4 hrs. at 10° C and left to stand overnight at 20° C, and the precipitate present was then filtered off, washed with tetrahydrofurane and dried.

Yield: 20.3 parts by wt. M.P.: 208° C.

NMR signals at τ = 2.25–3.0 (5H) and 5.9–6.7 ppm (4H) (dimethylsulphoxide-d₆).

Calculated: C 53.5, H 4.0, Cl 15.8, N 12.5, Found: C 53.6, H 4.3, Cl 16.1, N 11.8.

EXAMPLE 19

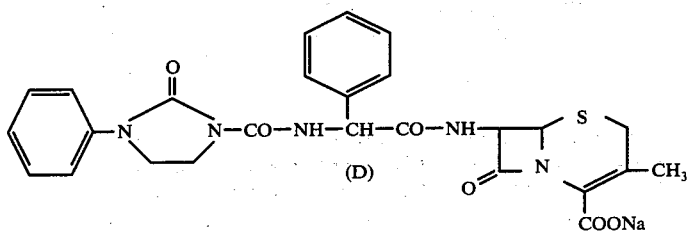

Sodium 7-{D-α-[(2-oxo-3-phenyl-imidazolidin-1-yl)-carbonylamino]-phenylacetamido}-3-methyl-ceph-3-em-4-carboxylate was obtained in the manner described in the preceding example from 2.5 parts by wt. of cephalexin hydrate and 1.54 parts by wt. of 1-chlorocarbonyl-2-oxo-3-phenyl-imidazolidine, initially as the free acid and then as the sodium salt in a yield of 3.5 parts by wt.

IR bands (in the carbonyl region) at: 1,755, 1,720, 1,670, 1,595 and 1,530 cm⁻¹ (Nujol).

The substance is crystalline and is in the form of the dihydrate. This was taken into account in the calculated analytical data:

Calculated: C 52.6, H 4.7, N 11.8, S 5.4, Found: C 52.6, H 4.7, N 12.0, S 5.4.

EXAMPLE 20

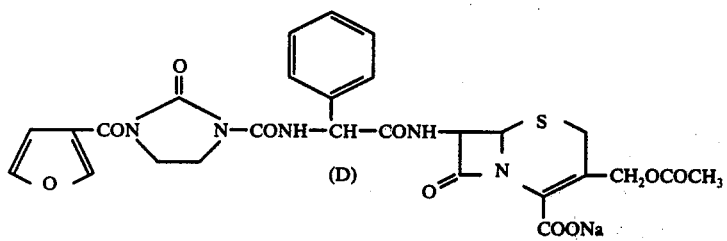

Sodium 7-{D-α-[(2-oxo-3-furoyl(3)-imidazolidin-1-yl)-carbonylamino]-phenylacetamido}-3-acetoxymethyl-ceph-3-em-4-carboxylate was prepared in 87% yield from 0.9 parts by weight of 1-chloro-carbonyl-2-oxo-3-furoyl(3)-imidazolidine and 1.5 parts by weight of cephaloglycine dihydrate, in a manner analogous to that described in Example 1.

IR bands at 3.290, 1.770, 1.738, 1.675, 1.640, 1.610, 1.525, 1.340, 1.253, 1.230, 1.195, 1.115 and 1.025 cm⁻¹.

NMR signals at τ = 0.5 (1H); 0.95 (1H); 1.6 (1H); 2.2 (1H); 2.3 -2.8 (%H); 3.1 (1H); 4.1 − 4.5 (2H); 5.0 (3H); 6.1 (4H); 6.65 (2H) and 7.95 ppm (3H) (in DMSO-d₆).

β-lactam content, according to NMR- and IR-spectrum: 92.5%.

The 1-chlorocarbonyl-2-oxo-3-furoyl(3)-imidazolidine, m.p. 130° C, used as the starting material was prepared from 1-furoyl (3)-2-oxo-imidazolidine (in turn prepared from 2-oxo-imidazolidine and 3-chlorocarbonylfuran) and phosgene in tetrahydrofuran in the presence of triethylamine.

EXAMPLE 21

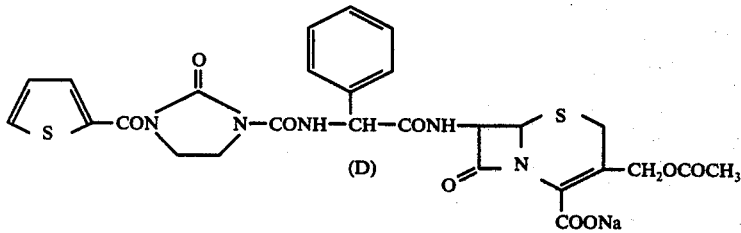

Sodium-7-{D-α-[(2-oxo-3-thienyl(2)carbonyl-imidazolidin-1-yl-carbonylamino]-phenylacetamido}-3-acetoxymethyl-ceph-3-em-4-carboxylate was prepared in 80% yield from 0.96 parts by weight of 1-chlorocarbonyl-2-oxo-3-thienyl(2)-carbonyl-imidazolidine and 1.5 parts by weight of cephaloglycine dihydrate, in a manner analogous to that described in Example 1.

IR bands at 3.450, 3.280, 3.190, 1.765, 1.730, 1.660, 1.598, 1.505, 1.360, 1.235, 1.105, 1.060, 1.020, 765 − 714 and 693 cm⁻¹.

NMR signals at τ = 2.15 (2H); 2.3 − 2.8 (5H); 2.85 (1H); 4.2 − 5.1 (5H); 6.05 (4H); 6.4 (1H); 6.8 (1H) and 7.8 ppm (3H) (in CD₃OD).

β-Lactam content, according to NMR- and IR-spectra: 92%.

The 1-chlorocarbonyl-2-oxo-3-thienyl(2)-carbonyl-imidazolidine, m.p. 130° C, used as the starting compound was prepared from 1-thienyl(2)-carbonyl-2-oxo-imidazolidine (in turn prepared from 2-oxo-imidazolidine and 2-chlorocarbonyl-thiophene) and phosgene in tetrahydrofuran in the presence of triethylamine.

EXAMPLE 22

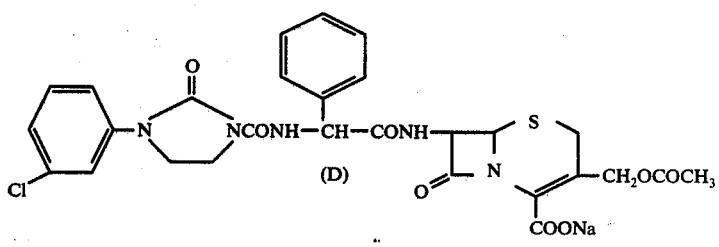

Sodium-7-{D-α-[(2-oxo-3-m-chlorophenyl-imidazolidin-1-yl)-carbonylamino]-phenylacetamido}-3-acetoxymethyl-ceph-3-em-4-carboxylate was prepared in a yield of 2.1 parts by weight from 1.5 parts by weight of cephaloglycine dihydrate and 0.84 parts by weight of 1-chlorocarbonyl-2-oxo-3-m-chlorophenyl-imidazolidine in the manner described in Example 3.

IR bands (carbonyl region) at 1.755 (shoulder), 1.745 (shoulder), 1.700, 1.660 (shoulder), 1.595, 1.530 (shoulder) and 1.515 cm⁻¹.

β-Lactam content: 72%.

The 1-chlorocarbonyl-2-oxo-3-m-chlorophenyl-imidazolidine, m.p. 136° C, used as the starting compound, was prepared from 1-m-chlorophenyl-2-oxo-imidazolidine (prepared from m-chloroaniline and 1-chloro-2-isocyanato-ethane) and phosgene in tetrahydrofuran.

EXAMPLE 23

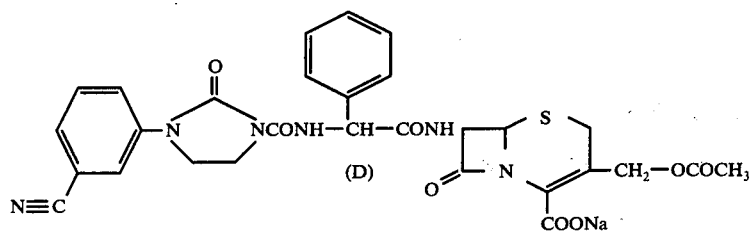

Sodium-7-{D-α-[(2-oxo-3-m-cyanophenyl-imidazolidine-1-yl)-carbonylamino]-phenylacetamido}-3-acetoxymethyl-ceph-3-em-4-carboxylate was prepared in a yield of 1.5 parts by weight from 1.5 parts by weight of cephaloglycine dihydrate and 0.81 parts by weight of 1-chlorocarbonyl-2-oxo-3-m-cyanophenyl-imidazolidine in the manner described in Example 3.

IR bands (carbonyl region) at 1.770 (shoulder), 1.745 (shoulder), 1.710, 1.655, 1.595 and 1.520 cm$^{-1}$.

β-Lactam content: 76%

The 1-chlorocarbonyl-2-oxo-3-m-cyanophenyl-imidazolidine, m.p. 170° C, used as the starting material was prepared from 1-m-cyanophenyl-2-oxo-imidazolidine (prepared from m-cyanoaniline and 1-chloro-2-isocyanatoethane) and phosgene in tetrahydrofuran.

EXAMPLE 24

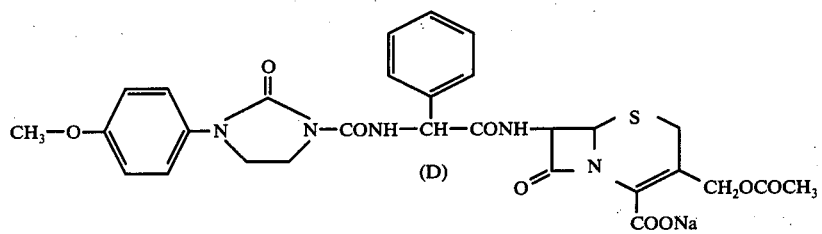

Sodium-7-{D-α-[(2-oxo-3-p-methoxyphenyl-imidazolidin-1-yl)-carbonylamino]-phenylacetamido}-3-acetoxymethyl-ceph-3-em-4-carboxylate was prepared in a yield of 1.8 parts by weight from 1.5 parts by weight of cephaloglycine dihydrate and 0.83 parts by weight of 1-chloro-carbonyl-2-oxo-3-p-methoxyphenyl-imidazolidine in the manner described in Example 3.

IR bands (carbonyl region) at 1.750, 1.700, 1.650, 1.585, 1.530 (shoulder), 1.520 (shoulder) and 1.500 cm$^{-1}$.

NMR signals at τ = 2.4 − 3.2 (m, 9H), 4.2 − 4.5 (m, 2H), 5.0 − 5.25 (m, 3H), 6.1 (s, 4H), 6.25 (s, 3H), 6.6 − 6.7 (2H) and 8.0 ppm (s, 3H) (in CD$_3$OD).

β-Lactam content: 74%.

The 1-chlorocarbonyl-2-oxo-3-p-methoxyphenyl-imidazolidine, m.p. 182° − 183° C, used as the starting material, was prepared from 1-p-methoxyphenyl-2-oxo-imidazolidine [prepared from 3-(4-methoxyanilino)propionic and hydrazide] and phosgene in tetrahydrofuran in the presence of triethylamine.

EXAMPLE 25

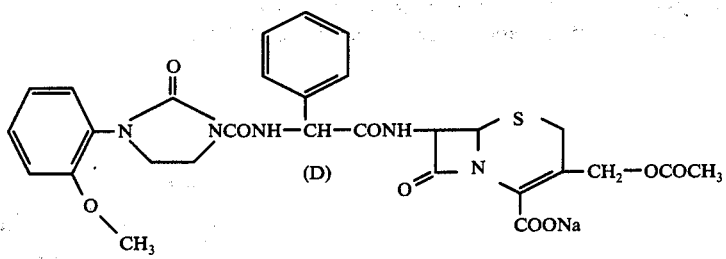

Sodium-7-{D-α-[(2-oxo-3-o-methoxyphenyl-imidazolidin-1-yl)-carbonylamino]-phenylacetamido}-3-acetoxy-methyl-ceph-3-em-4-carboxylate was prepared in a yield of 1.9 parts by weight from 1.5 parts by weight of cephaloglycine dihydrate and 0.82 parts by weight of 1-chlorocarbonyl-2-oxo-3-o-methoxyphenyl-imidazolidine in the manner described in Example 3.

IR bands (carbonyl region) at 1.750 (shoulder), 1.745, 1.710, 1.655, 1.595, 1.530 (shoulder), 1.515 and 1.485 cm$^{-1}$.

NMR-signals at τ = 2.4 − 3.0 (m, 9H), 4.3 (d, 1H), 4.4 (s, 1H), 4.95 − 5.2 (m, 3H), 6.1 (s, broad, 7H), 6.6 (2H) and 8.0 ppm (s, 3H) (in CD$_3$OD).

β-Lactam content: 69%.

The 1-chlorocarbonyl-2-oxo-3-o-methoxyphenyl-imidazolidine, m.p. 88° − 91° C, used as the starting material was prepared from 1-o-methoxyphenyl-2-oxo-imidazolidine [prepared from 3-(2-methoxyanilino)propionic acid hydrazide] and phosgene in tetrahydrofuran in the presence of triethylamine.

EXAMPLE 26

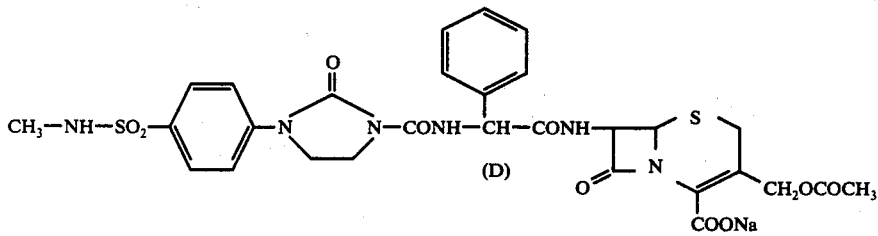

Sodium-7-{D-α-[(2-oxo-3-p-methylaminosulfonyl-phenyl-imidazolidin-1-yl)-carbonylamino]-phenylacetamido}-3-acetoxymethyl-ceph-3-em-4-carboxylate was prepared in a yield of 1.7 parts by weight from 1.5 parts by weight of cephaloglycine dihydrate and 1.0 parts by weight of 1-chlorocarbonyl-2-oxo-3-p-methylamino-sulfonylphenyl-imidazolidine in the manner described in Example 3.

IR bands (carbonyl region) at 1.755 (shoulder), 1.750, 1.705, 1.650, 1.585, 1.530 (shoulder), and 1.520 cm$^{-1}$.

NMR signals at $\tau$ = 2.2 (s, 4H), 2.3 – 2.8 (m, 5H), 4.3 (d, 1H), 4.4 (s, 1H), 4.95 – 5.2 (m, 3H), 6.05 (s, broad, 4H), 6.6 (2H), 7.45 (s, 3H) and 8.0 ppm (s, 3H).

β-Lactam content: 90%.

The 1-chlorocarbonyl-2-oxo-3-p-methylaminosulfonylphenyl-imidazolidine, m.p. 194° – 195° C, used as the starting material, was prepared from 1-p-methylaminosulfonylphenyl-imidazolidine (prepared from 1-phenyl-2-oxo-imidazolidine and chlorosulfonic acid, followed by reaction with methylamine) and phosgene in phenyl cyanide.

EXAMPLE 27

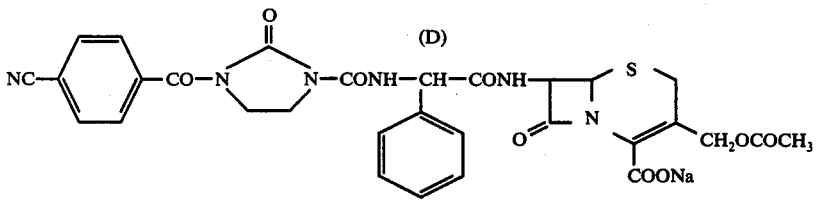

Sodium-7-{D-α-[(2-oxo-3-{4-cyanobenzoyl}-imidazolidin-1-yl)-carbonylamino]-phenylacetamido}-3-acetoxymethyl-ceph-3-em-4-carboxylate was prepared in 63% yield from 1.4 parts by weight of 1-chlorocarbonyl-2-oxo-3-(4-cyanobenzoyl)-imidazolidine and 2.3 parts by weight of cephaloglycine dihydrate, in the manner described in Example 3. Melting point (decomp.) 190° – 195° C.

IR bands at 2.230, 1.770, 1.740, 1.670, 1.600 cm$^{-1}$.

NMR signals at δ = 7.75 (4H), 7.35 (5H), 3.92 (4H) 2.00 (3H) in CD$_3$OD.

The 1-chlorocarbonyl-2-oxo-3-(4-cyanobenzoyl)-imidazolidine used as the starting material was prepared from 1-(4-cyanobenzoyl)-2-oxo-imidazolidine, m.p. 232° – 234° C, (prepared from 2-oxo-imidazolidine and 4-cyanobenzoylchloride) and phosgene in tetrahydrofuran in the presence of pyridine.

EXAMPLE 28

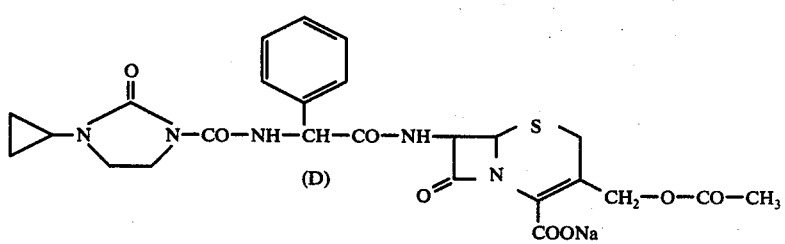

Sodium-7-{D-α-[(2-oxo-3-cyclopropyl-imidazolidin-1-yl)-carbonylamino]-phenylacetamido}-3-acetoxymethyl-ceph-3-em-4-carboxylate was prepared in a yield of 1.4 parts by weight from 1.5 parts by weight of cephaloglycine dihydrate and 0.6 parts by weight of 1-chlorocarbonyl-2-oxo-3-cyclopropyl-imidazolidine in the manner described in Example 3.

IR bands (carbonyl region) at 1.770, 1.710, 1.600 and 1.515 cm$^{-1}$.

β-Lactam content: 78%.

NMR signals at $\tau$ = 2.3 – 2.8 (5H), 4.2 – 4.35 (d, 2H), 4.45 (s, 1H), 4.9 – 5.2 (3H), 6.2 – 6.7 (m, 6H), 7.3 – 7.7 (m, 1H), and 9.25 ppm (d, 2H) (in CD$_3$OD).

The 1-chlorocarbonyl-2-oxo-3-(4-cyanobenzoyl)-imidazolidine used as the starting material was prepared from 1-(4-cyanobenzoyl)-2-oxo-imidazolidine, m.p. 232° – 234° C, (prepared from 2-oxo-imidazolidine and 4-cyanobenzoylchloride) and phosgene in tetrahydrofuran in the presence of pyridine.

What is claimed is:

1. A compound selected from the group consisting of a cephalosporin derivative of the formula:

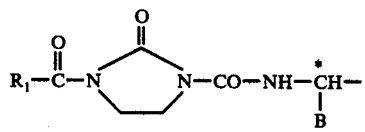

-continued

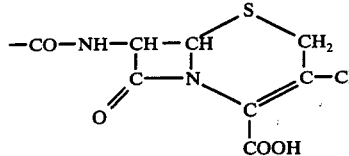

the nontoxic salts thereof and the hydrates thereof wherein the carbon atom designated * constitutes a center of chirality;

E is hydrogen; hydroxy or acetoxy;

B is phenyl; methylphenyl; chlorophenyl; hydroxyphenyl; or cyclohexa-1,4-dien-1-yl; and $R_1$ is phenyl; naphthyl; phenyl or naphthyl substituted by one to five substituents selected from the group consisting of halo, cyano, alkyl of 1 to 4 carbon atoms, alkoxy of 1 to 4 carbon atoms and alkylsulfamyl of 1 to 4 carbon atoms; thienyl; furyl; piperidyl; pyrrolidyl; NC—CH$_2$—; NC—CH$_2$-CH$_2$; or H$_3$CO—.

2. A compound according to claim 1, wherein E is acetoxy.

3. A compound according to claim 1, wherein $R_1$ is phenyl; naphthyl; or phenyl or naphthyl substituted by one to five substituents selected from the group consisting of halo, cyano, alkyl of 1 to 4 carbon atoms and alkylsulfamyl of 1 to 4 carbon atoms.

4. A compound according to claim 1, wherein $R_1$ is thienyl, furyl, piperidyl or pyrrolidyl.

5. The compound according to claim 1, which is 7-D-α-[2-oxo-3-cyanoacetyl-imidazolidin-1-yl)-carbonyl-amino]-phenylacetamido-3-acetoxymethyl-ceph-3-em-4-carboxylic acid, or the sodium salt thereof.

6. The compound according to claim 1, which is 7-D-α-[(2-oxo-3-β-cyanopropionyl-imidazolidin-1-yl)-carbonylamino]-phenylacetamido-3-acetamido-3-acetoxymethyl-ceph-3-em-4-carboxylic acid, or the sodium salt thereof.

7. The compound according to claim 1, which is 7-D-α-[(2-oxo-3-methoxycarbonyl-imidazolidin-1-yl)-carbonylamino]-phenylacetamido-3-acetoxymethyl-ceph-3-em-4-carboxylic acid, or the sodium salt thereof.

8. The compound according to claim 1, which is 7-{D-α-[(2-oxo-3-benzoyl-imidazolidin-1-yl)-carbonylamino]-phenylacetamido}-3-acetoxymethyl-ceph-3-em-4-carboxylic acid, or the sodium salt thereof.

9. The compound according to claim 1, which is 7-{D-α-[(2-oxo-3-furoyl-(2)-imidazolidin-1-yl)-carbonylamino]-phenylacetamido}-3-acetoxymethyl-ceph-3-em-4-carboxylic acid, or the sodium salt thereof.

10. The compound according to claim 1, which is 7-{D-α-[(2-oxo-3-benzoyl-imidazolidin-1-yl)-carbonylamino]-phenylacetamido}-3-methyl-ceph-3-em-4-carboxylic acid, or the sodium salt thereof.

11. The compound according to claim 1, which is sodium 7-{D-α-[(2-oxo-3-furoyl(3)-imidazolidin-1-yl)-carbonylamino]-phenylacetamido}-3-em-4-carboxylate.

12. The compound according to claim 1, which is sodium-7-{D-α-[(2-oxo-3-thienyl(2)carbonyl-imidazolidin-1-yl-carbonyamino]-phenylacetamido}-3-acetoxymethyl-ceph-3-em-4-carboxylate.

13. The compound according to claim 1, which is sodium 7-{D-α-[(2-oxo-3-{4-cyanobenzoyl}-imidazolidin-1-yl)-carbonylamino]-phenylacetamido}-3-acetoxymethyl-ceph-3-em-4-carboxylate.

14. A pharmaceutical composition useful for treating bacterial infections in humans and animals which comprises an antibacterially-effective amount of a compound of claim 1 in combination with a pharmaceutically acceptable nontoxic, inert diluent or carrier.

15. A method of treating bacterial infections in humans and animals which comprises administering to such human or animal an antibacterially-effective amount of a compound of claim 1.

16. A pharmaceutical composition useful for treating bacterial infections in humans and animals which comprises an antibacterially-effective amount of a compound of claim 1 in combination with an antibacterially-effective amount of a compound selected from the group consisting of Gentamicin, Sisomicin, Kanamicin, Amikacin and Tobramicin, in combination with a pharmaceutically acceptable nontoxic, inert diluent or carrier.

17. A method of treating bacterial infections in humans and animals which comprises administering an antibacterially-effective amount of a compound of claim 1 in combination with an antibacterially-effective amount of a compound selected from the group consisting of Gentamicin, Sisomicin, Kanamicin, Amikacin and Tobramicin.

18. An animal feedstuff which comprises an antibacterially-effective amount of a compound of claim 1 in combination with nutritious material.

19. A growth-promoting composition which comprise an antibacterially-effective amount of a compound of claim 1 in combination with an edible material.

20. A method of promoting growth in animals which comprises administering to said animal a growth-promoting amount of a compound of claim 1.

* * * * *